US005470712A

United States Patent [19]

Simpson et al.

[11] Patent Number: 5,470,712
[45] Date of Patent: Nov. 28, 1995

[54] ANTIGENIC PROTEINS OF BORRELIA BURGDORFERI

[76] Inventors: Warren Simpson, 713 S. Second St.; T. G. Schwan, 601 S. 5th St., both of Hamilton, Mont. 59840

[21] Appl. No.: 20,245

[22] Filed: Feb. 19, 1993

Related U.S. Application Data

[63] Continuation of Ser. No. 664,731, Mar. 5, 1991, abandoned, which is a continuation-in-part of Ser. No. 487,716, Mar. 5, 1990, abandoned.

[51] Int. Cl.[6] .................................................. G01N 33/569

[52] U.S. Cl. ......................... 435/7.32; 435/970; 435/975; 435/71.2; 435/320.1; 530/350; 530/810; 530/825; 536/23.7

[58] Field of Search .................................. 435/7.32, 970, 435/975, 243, 317.1, 71.1, 71.2, 320.1; 436/518, 808, 810; 530/350, 388.4, 387.9, 389.1, 389.5, 825, 810, 811, 812, 825; 536/23.7

[56] References Cited

U.S. PATENT DOCUMENTS 4,888,276 12/1989 Shelburne .............................. 435/7.32

OTHER PUBLICATIONS

Nadal et al, "Immunoblot Analysis of Antibody Binding to Polypeptides of *Borrelia burgdorferi* in Children with Different Clinical Manifestations of Lyme Disease", Ped. Res., 26(4):377–382 (1989).

Simpson et al. "Reactivity of Human Lyme Borreliosis sera with a 39–kilodalton Antigen Specific to *Borrelia burgdorferi*", J. Clin. Microbiol., 28(6):1329–1337 (Jun. 1990).

Wallich et al, Infect. Immun., 58(6):1711–1719 (Jun. 1990).

Magnarelli et al, J. Inf. Dis. 159(1):43–49 (Jan. 1989).

Hansen et al., J. Clin. Microbiol. 26(2):338–346 (Feb. 1988).

Grodzicki et al, J. Inf. Dis. 157(4):790–797 (Apr. 1988).

Cunningham et al, Ann. N.Y. Acad. Sci. 539:376–378 (1988).

Barbour, Clin. Microbiol. Rev. 1(4):399–414 (Oct. 1988).

Benach et al, J. Immunol. 140(1):265–272 (Jan. 1, 1988).

*Primary Examiner*—Carol E. Bidwell
*Attorney, Agent, or Firm*—Morgan & Finnegan

[57] ABSTRACT

The present invention relates to antigenic proteins specific to *Borrelia burgdorferi* which have a molecular weight of 28 kDa or 39 kDa as determined by SDS-PAGE and are reactivity with Lyme borreliosis serum or fragments thereof and to the corresponding DNA. The proteins, especially the 39 kDa proteins ($\alpha$ and $\beta$) can be used to diagnosis mammals previously or currently infected with the Lyme borreliosis causing agent.

17 Claims, 14 Drawing Sheets

A.

B.

| 1 | | | | 5 | | | | | 10 | | | | | 15 | | | | | |
|---|---|---|---|---|---|---|---|---|---|---|---|---|---|---|---|---|---|---|---|
| Met | Asn | Lys | Ile | Leu | Leu | Leu | Ile | Leu | Leu | Glu | Ser | Ile | Val | Phe | Leu | Ser | **Cys** | Ser | GENE 1 |
| Met | Arg | Ile | Val | Ile | Phe | Ile | Phe | Gly | Ile | Leu | **Leu** | Thr | Ser | **Cys** | Phe | Ser | Arg | Asn | GENE 2 |
| Met | Lys | Lys | Tyr | Leu | Leu | Gly | Ile | Gly | Leu | Ile | Leu | Ala | **Leu** | Ile | Ala | **Cys** | Lys | Gln | OspA |
| Met | Arg | Leu | Leu | Ile | Gly | Phe | Ala | Leu | Ala | Leu | Ala | **Leu** | Ile | Gly | **Cys** | Ala | Gln | Lys | OspB |

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 2304
( B ) TYPE: nucleic acid
( C ) STRANDEDNESS: both
( D ) TOPOLOGY: unknown ( i i ) MOLECULE TYPE: genomic DNA ( i i i ) HYPOTHETICAL: No ( v i ) ORIGINAL SOURCE:
( A ) ORGANISM: Borrelia burgdorferi
( B ) STRAIN: Sh-2-82
( C ) INDIVIDUAL ISOLATE: Sh-2-82, P- 6
( D ) DEVELOPMENTAL STAGE:
( E ) HAPLOTYPE:
( F ) TISSUE TYPE:
( G ) CELL TYPE:

-continued ( H ) CELL LINE:
( I ) ORGANELLE:

( i x ) FEATURE:
( A ) NAME/KEY: pSPR45
( B ) LOCATION:
( C ) IDENTIFICATION METHOD: By experiment
( D ) OTHER INFORMATION: cDNA containing coding regions for p39α and p39β.

( x i ) SEQUENCE DESCRIPTION: SEQ ID NO:1:

```
TCCTGATAGT GAATATGCAT TTGATTTATT TAAATCAAAG    40
TTATAAACTA CTAAATATAG CTTTGTTTGT AAAGGGGAAA    80
TAGTTTATGA ATAAAATATT GTTGTTGATT TTGCTTGAGA   120
GTATTGTTTT TTTATCTTGT AGTGGTAAAG GTAGTCTTGG   160
GAGCGAAATT CCTAAGGTAT CTTTAATAAT TGATGGAACT   200
TTTGATGATA AATCTTTTAA TGAGAGTGCT TTAAATGGCG   240
TAAAAAAAGT TAAAGAAGAA TTTAAAATTG AGCTTGTTTT   280
AAAAGAATCC TCATCAAATT CTTATTTATC TGATCTTGAA   320
GGGCTTAAGG ATGCGGGCTC AGATTTAATT TGGCTTATTG   360
GGTATAGATT TAGCGATGTG GCCAAGGTTG CGGCTCTTCA   400
AAATCCCGAT ATGAAATATG CAATTATTGA TCCTATTTAT   440
TCTAACGATC CTATTCCTGC AAATTTGGTG GGCATGACCT   480
TTAGAGCTCA AGAGGGTGCA TTTTTAACGG GTTATATTGC   520
TGCAAAACTT TCTAAAACAG GTAAAATTGG ATTTTTAGGG   560
GGAATAGAAG GCGAGATAGT AGATGCTTTT AGGTATGGGT   600
ATGAAGCTGG TGCTAAGTAT GCTAATAAAG ATATAAAGAT   640
ATCTACTCAG TATATTGGTA GTTTTGCTGA CCTTGAAGCT   680
GGTAGAAGCG TTGCAACTAG AATGTATTCT GATGAGATAG   720
ACATTATTCA TCATGCTGCA GGCCTTGGAG GAATTGGGGC   760
TATTGAGGTT GCAAAAGAAC TTGGTTCTGG GCATTACATT   800
ATTGGAGTTG ATGAAGATCA AGCATATCTT GCTCCTGACA   840
ATGTAATAAC ATCTACAACT AAAGATGTTG GTAGAGCTTT   880
AAATATTTTT ACATCTAACC ATTTAAAAAC TAATACTTTC   920
GAAGGTGGCA AATTAATAAA TTATGGCCTT AAAGAAGGAG   960
TTGTGGGGTT TGTAAGAAAT CCTAAAATGA TTTCCTTTGA  1000
ACTTGAAAAA GAAATTGACA ATCTTTCTAG CAAAATAATC  1040
AACAAAGAAA TTATTGTTCC ATCTAATAAA GAAAGTTATG  1080
AGAAGTTTCT TAAAGAATTT ATTTAAATAA AGAATCAATT  1120
TATATATTTT ATTTTTAAGT ATAAAAAACA CATTGGTTTT  1160
GTTTGAATAA TTGAAATGGA GAAGTGCTTT ATATGAGAAT  1200
TGTAATTTTT ATATTCGGTA TTTTGTTGAC TTCTTGCTTT  1240
AGTAGAAATG GAATAGAATC TAGTTCAAAA AAAATTAAGA  1280
TATCCATGTT GGTAGATGGT GTTCTTGACG ACAAATCTTT  1320
TAATTCTAGT GCTAATGAGG CTTTATTACG CTTGAAAAAA  1360
```

-continued

| | | | | |
|---|---|---|---|---|
| GATTTTCCAG | AAAATATTGA | AGAAGTTTTT | TCTTGTGCTA | 1400 |
| TTTCTGGAGT | TTATTCTAGT | TATGTTTCAG | ATCTTGATAA | 1440 |
| TTTAAAAAGG | AATGGCTCAG | ACTTGATTTG | GCTTGTAGGG | 1480 |
| TACATGCTTA | CGGATGCATC | TTTATTGGTT | TCATCGGAGA | 1520 |
| ATCCAAAAAT | TAGCTATGGA | ATAATAGATC | CCATTTATGG | 1560 |
| TGATGATGTT | CAGATTCCTG | AAAACTTGAT | TGCTGTTGTT | 1600 |
| TTCAGAGTAG | AGCAAGGTGC | TTTTTTGGCT | GGCTATATTG | 1640 |
| CAGCCAAAAA | AAGCTTTTCT | GGCAAAATAG | GTTTTATAGG | 1680 |
| GGGAATGAAG | GGTAATATAG | TAGATGCATT | TCGCTATGGT | 1720 |
| TATGAATCTG | GAGCAAAGTA | TGCTAATAAA | GATATAGAGA | 1760 |
| TTATAAGTGA | ATATTCCAAT | TCTTTTTCCG | ATGTTGATAT | 1800 |
| TGGTAGAACC | ATAGCTAGTA | AAATGTATTC | TAAAGGGATA | 1840 |
| GATGTAATTC | ATTTTGCAGC | TGGTTTAGCA | GGAATTGGTG | 1880 |
| TTATTGAGGC | AGCAAAAAAC | CTTGGCGATG | GTTACTATGT | 1920 |
| TATTGGAGCC | GATCAGGATC | AGTCATATCT | TGCTCCTAAA | 1960 |
| AATTTTATTA | CTTCTGTTAT | AAAAAACATT | GGGGACGCAT | 2000 |
| TGTATTTGAT | TACTGGCGAA | TATATTAAAA | ATAATAATGT | 2040 |
| TTGGGAAGGT | GGAAAAGTTG | TTCAAATGGG | ATTAAGAGAT | 2080 |
| GGTGTTATTG | GGCTGCCTAA | TGCGAATGAA | TTTGAATACA | 2120 |
| TAAAAGTTCT | TGAGAGAAAA | ATAGTCAATA | AAGAGATCAT | 2160 |
| TGTTCCTTGC | AATCAGGAGG | AATATGAAAT | TTTTATAAAA | 2200 |
| CAAATATTAA | AGTTATAAAC | TTTTGAAATA | GAAAGATTTT | 2240 |
| AATTTTCCAG | TTTTTAATTT | TTTAATTATG | TTATATTTAT | 2280 |
| TGTGTTATAA | TAAATAGAAG | TACA | | 2304 |

( 2 ) INFORMATION FOR SEQ ID NO:2:

( i ) SEQUENCE CHARACTERISTICS:
( A ) LENGTH: 1106
( B ) TYPE: nucleic acid
( C ) STRANDEDNESS: double
( D ) TOPOLOGY: unknown ( i i ) MOLECULE TYPE: genomic DNA ( i i i ) HYPOTHETICAL: No ( v i ) ORIGINAL SOURCE:
( A ) ORGANISM: Borrelia burgdorferi
( B ) STRAIN: Sh-2-82
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION:
( C ) IDENTIFICATION METHOD: By experiment
( D ) OTHER INFORMATION: Gene encoding p39α.

-continued ( x i ) SEQUENCE DESCRIPTION: SEQ ID NO:2:

```
TCCTGATAGT GAATATGCAT TTGATTTATT TAAATCAAAG                40

TTATAAACTA CTAAATATAG CTTTGTTTGT AAAGGGGAAA                80

TAGTTT ATG AAT AAA ATA TTG TTG TTG ATT TTG CTT            116
       Met Asn Lys Ile Leu Leu Leu Ile Leu Leu
        1               5                  10

GAG AGT ATT GTT TTT TTA TCT TGT AGT GGT AAA GGT           152
Glu Ser Ile Val Phe Leu Ser Cys Ser Gly Lys Gly
                15                  20

AGT CTT GGG AGC GAA ATT CCT AAG GTA TCT TTA ATA           188
Ser Leu Gly Ser Glu Ile Pro Lys Val Ser Leu Ile
         25                  30

ATT GAT GGA ACT TTT GAT GAT AAA TCT TTT AAT GAG           224
Ile Asp Gly Thr Phe Asp Asp Lys Ser Phe Asn Glu
35                   40                  45

AGT GCT TTA AAT GGC GTA AAA AAA GTT AAA GAA GAA           260
Ser Ala Leu Asn Gly Val Lys Lys Val Lys Glu Glu
             50                  55

TTT AAA ATT GAG CTT GTT TTA AAA GAA TCC TCA TCA           296
Phe Lys Ile Glu Leu Val Leu Lys Glu Ser Ser Ser
     60                  65                  70

AAT TCT TAT TTA TCT GAT CTT GAA GGG CTT AAG GAT           332
Asn Ser Tyr Leu Ser Asp Leu Glu Gly Leu Lys Asp
                 75                  80

GCG GGC TCA GAT TTA ATT TGG CTT ATT GGG TAT AGA           368
Ala Gly Ser Asp Leu Ile Trp Leu Ile Gly Tyr Arg
         85                  90

TTT AGC GAT GTG GCC AAG GTT GCG GCT CTT CAA AAT           404
Phe Ser Asp Val Ala Lys Val Ala Ala Leu Gln Asn
 95                 100                 105

CCC GAT ATG AAA TAT GCA ATT ATT GAT CCT ATT TAT           440
Pro Asp Met Lys Tyr Ala Ile Ile Asp Pro Ile Tyr
            110                 115

TCT AAC GAT CCT ATT CCT GCA AAT TTG GTG GGC ATG           476
Ser Asn Asp Pro Ile Pro Ala Asn Leu Val Gly Met
    120                 125                 130

ACC TTT AGA GCT CAA GAG GGT GCA TTT TTA ACG GGT           512
Thr Phe Arg Ala Gln Glu Gly Ala Phe Leu Thr Gly
                135                 140

TAT ATT GCT GCA AAA CTT TCT AAA ACA GGT AAA ATT           548
Tyr Ile Ala Ala Lys Leu Ser Lys Thr Gly Lys Ile
        145                 150

GGA TTT TTA GGG GGA ATA GAA GGC GAG ATA GTA GAT           584
Gly Phe Leu Gly Gly Ile Glu Gly Glu Ile Val Asp
155                 160                 165

GCT TTT AGG TAT GGG TAT GAA GCT GGT GCT AAG TAT           620
Ala Phe Arg Tyr Gly Tyr Glu Ala Gly Ala Lys Tyr
            170                 175

GCT AAT AAA GAT ATA AAG ATA TCT ACT CAG TAT ATT           656
Ala Asn Lys Asp Ile Lys Ile Ser Thr Gln Tyr Ile
    180                 185                 190

GGT AGT TTT GCT GAC CTT GAA GCT GGT AGA AGC GTT           692
Gly Ser Phe Ala Asp Leu Glu Ala Gly Arg Ser Val
                195                 200

GCA ACT AGA ATG TAT TCT GAT GAG ATA GAC ATT ATT           728
Ala Thr Arg Met Tyr Ser Asp Glu Ile Asp Ile Ile
        205                 210

CAT CAT GCT GCA GGC CTT GGA GGA ATT GGG GCT ATT           764
```

-continued

His His Ala Ala Gly Leu Gly Gly Ile Gly Ala Ile
215 220 225

GAG GTT GCA AAA GAA CTT GGT TCT GGG CAT TAC ATT 800
Glu Val Ala Lys Glu Leu Gly Ser Gly His Tyr Ile
230 235

ATT GGA GTT GAT GAA GAT CAA GCA TAT CTT GCT CCT 836
Ile Gly Val Asp Glu Asp Gln Ala Tyr Leu Ala Pro
240 245 250

GAC AAT GTA ATA ACA TCT ACA ACT AAA GAT GTT GGT 872
Asp Asn Val Ile Thr Ser Thr Thr Lys Asp Val Gly
255 260

AGA GCT TTA AAT ATT TTT ACA TCT AAC CAT TTA AAA 908
Arg Ala Leu Asn Ile Phe Thr Ser Asn His Leu Lys
265 270

ACT AAT ACT TTC GAA GGT GGC AAA TTA ATA AAT TAT 944
Thr Asn Thr Phe Glu Gly Gly Lys Leu Ile Asn Tyr
275 280 285

GGC CTT AAA GAA GGA GTT GTG GGG TTT GTA AGA AAT 980
Gly Leu Lys Glu Gly Val Val Gly Phe Val Arg Asn
290 295

CCT AAA ATG ATT TCC TTT GAA CTT GAA AAA GAA ATT 1016
Pro Lys Met Ile Ser Phe Glu Leu Glu Lys Glu Ile
300 305 310

GAC AAT CTT TCT AGC AAA ATA ATC AAC AAA GAA ATT 1052
Asp Asn Leu Ser Ser Lys Ile Ile Asn Lys Glu Ile
315 320

ATT GTT CCA TCT AAT AAA GAA AGT TAT GAG AAG TTT 1088
Ile Val Pro Ser Asn Lys Glu Ser Tyr Glu Lys Phe
325 330

CTT AAA GAA TTT ATT TAA 1106
Leu Lys Glu Phe Ile
335

( 2 ) INFORMATION FOR SEQ ID NO:3:

( i ) SEQUENCE CHARACTERISTICS:
( A ) LENGTH: 1198
( B ) TYPE: nucleic acid
( C ) STRANDEDNESS: double
( D ) TOPOLOGY: unknown ( i i ) MOLECULE TYPE: genomic DNA ( i i i ) HYPOTHETICAL: No ( v i ) ORIGINAL SOURCE:
( A ) ORGANISM: Borrelia burgdorferi
( B ) STRAIN: Sh-2-82
( C ) INDIVIDUAL ISOLATE: Sh-2-82, P- 6
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION:
( C ) IDENTIFICATION METHOD:
( D ) OTHER INFORMATION: Gene encoding p39β.

( x i ) SEQUENCE DESCRIPTION: SEQ ID NO:3:

ATAAAGAATC AATTTATATA TTTTATTTTT AAGTATAAAA 40

AACACATTGG TTTTGTTTGA ATAATTGAAA TGGAGAAGTG 80

-continued

```
CTTTAT    ATG  AGA  ATT  GTA  ATT  TTT  ATA  TTC  GGT  ATT       116
          Met  Arg  Ile  Val  Ile  Phe  Ile  Phe  Gly  Ile
           1                   5                        10

TTG  TTG  ACT  TCT  TGC  TTT  AGT  AGA  AAT  GGA  ATA  GAA       152
Leu  Leu  Thr  Ser  Cys  Phe  Ser  Arg  Asn  Gly  Ile  Glu
                     15                       20

TCT  AGT  TCA  AAA  AAA  ATT  AAG  ATA  TCC  ATG  TTG  GTA       188
Ser  Ser  Ser  Lys  Lys  Ile  Lys  Ile  Ser  Met  Leu  Val
           25                       30

GAT  GGT  GTT  CTT  GAC  GAC  AAA  TCT  TTT  AAT  TCT  AGT       224
Asp  Gly  Val  Leu  Asp  Asp  Lys  Ser  Phe  Asn  Ser  Ser
35                        40                       45

GCT  AAT  GAG  GCT  TTA  TTA  CGC  TTG  AAA  AAA  GAT  TTT       260
Ala  Asn  Glu  Ala  Leu  Leu  Arg  Leu  Lys  Lys  Asp  Phe
                50                       55

CCA  GAA  AAT  ATT  GAA  GAA  GTT  TTT  TCT  TGT  GCT  ATT       296
Pro  Glu  Asn  Ile  Glu  Glu  Val  Phe  Ser  Cys  Ala  Ile
      60                       65                       70

TCT  GGA  GTT  TAT  TCT  AGT  TAT  GTT  TCA  GAT  CTT  GAT       332
Ser  Gly  Val  Tyr  Ser  Ser  Tyr  Val  Ser  Asp  Leu  Asp
                     75                       80

AAT  TTA  AAA  AGG  AAT  GGC  TCA  GAC  TTG  ATT  TGG  CTT       368
Asn  Leu  Lys  Arg  Asn  Gly  Ser  Asp  Leu  Ile  Trp  Leu
           85                       90

GTA  GGG  TAC  ATG  CTT  ACG  GAT  GCA  TCT  TTA  TTG  GTT       404
Val  Gly  Tyr  Met  Leu  Thr  Asp  Ala  Ser  Leu  Leu  Val
95                       100                      105

TCA  TCG  GAG  AAT  CCA  AAA  ATT  AGC  TAT  GGA  ATA  ATA       440
Ser  Ser  Glu  Asn  Pro  Lys  Ile  Ser  Tyr  Gly  Ile  Ile
               110                      115

GAT  CCC  ATT  TAT  GGT  GAT  GAT  GTT  CAG  ATT  CCT  GAA       476
Asp  Pro  Ile  Tyr  Gly  Asp  Asp  Val  Gln  Ile  Pro  Glu
     120                      125                      130

AAC  TTG  ATT  GCT  GTT  GTT  TTC  AGA  GTA  GAG  CAA  GGT       512
Asn  Leu  Ile  Ala  Val  Val  Phe  Arg  Val  Glu  Gln  Gly
                    135                      140

GCT  TTT  TTG  GCT  GGC  TAT  ATT  GCA  GCC  AAA  AAA  AGC       548
Ala  Phe  Leu  Ala  Gly  Tyr  Ile  Ala  Ala  Lys  Lys  Ser
          145                      150

TTT  TCT  GGC  AAA  ATA  GGT  TTT  ATA  GGG  GGA  ATG  AAG       584
Phe  Ser  Gly  Lys  Ile  Gly  Phe  Ile  Gly  Gly  Met  Lys
155                      160                      165

GGT  AAT  ATA  GTA  GAT  GCA  TTT  CGC  TAT  GGT  TAT  GAA       620
Gly  Asn  Ile  Val  Asp  Ala  Phe  Arg  Tyr  Gly  Tyr  Glu
               170                      175

TCT  GGA  GCA  AAG  TAT  GCT  AAT  AAA  GAT  ATA  GAG  ATT       656
Ser  Gly  Ala  Lys  Tyr  Ala  Asn  Lys  Asp  Ile  Glu  Ile
     180                      185                      190

ATA  AGT  GAA  TAT  TCC  AAT  TCT  TTT  TCC  GAT  GTT  GAT       692
Ile  Ser  Glu  Tyr  Ser  Asn  Ser  Phe  Ser  Asp  Val  Asp
                    195                      200

ATT  GGT  AGA  ACC  ATA  GCT  AGT  AAA  ATG  TAT  TCT  AAA       728
Ile  Gly  Arg  Thr  Ile  Ala  Ser  Lys  Met  Tyr  Ser  Lys
          205                      210

GGG  ATA  GAT  GTA  ATT  CAT  TTT  GCA  GCT  GGT  TTA  GCA       764
Gly  Ile  Asp  Val  Ile  His  Phe  Ala  Ala  Gly  Leu  Ala
215                      220                      225

GGA  ATT  GGT  GTT  ATT  GAG  GCA  GCA  AAA  AAC  CTT  GGC       800
Gly  Ile  Gly  Val  Ile  Glu  Ala  Ala  Lys  Asn  Leu  Gly
               230                      235
```

-continued

```
GAT GGT TAC TAT GTT ATT GGA GCC GAT CAG GAT CAG          836
Asp Gly Tyr Tyr Val Ile Gly Ala Asp Gln Asp Gln
    240                 245                 250

TCA TAT CTT GCT CCT AAA AAT TTT ATT ACT TCT GTT          872
Ser Tyr Leu Ala Pro Lys Asn Phe Ile Thr Ser Val
                255                 260

ATA AAA AAC ATT GGG GAC GCA TTG TAT TTG ATT ACT          908
Ile Lys Asn Ile Gly Asp Ala Leu Tyr Leu Ile Thr
        265                 270

GGC GAA TAT ATT AAA AAT AAT AAT GTT TGG GAA GGT          944
Gly Glu Tyr Ile Lys Asn Asn Asn Val Trp Glu Gly
275                 280                 285

GGA AAA GTT GTT CAA ATG GGA TTA AGA GAT GGT GTT          980
Gly Lys Val Val Gln Met Gly Leu Arg Asp Gly Val
            290                 295

ATT GGG CTG CCT AAT GCG AAT GAA TTT GAA TAC ATA         1016
Ile Gly Leu Pro Asn Ala Asn Glu Phe Glu Tyr Ile
    300                 305                 310

AAA GTT CTT GAG AGA AAA ATA GTC AAT AAA GAG ATC         1052
Lys Val Leu Glu Arg Lys Ile Val Asn Lys Glu Ile
                315                 320

ATT GTT CCT TGC AAT CAG GAG GAA TAT GAA ATT TTT         1088
Ile Val Pro Cys Asn Gln Glu Glu Tyr Glu Ile Phe
        325                 330

ATA AAA CAA ATA TTA AAG TTA TAA ACTTTTGA                1120
Ile Lys Gln Ile Leu Lys Leu
335                 340

AATAGAAAGA TTTTAATTTT CCAGTTTTTA ATTTTTTAAT             1160

TATGTTATAT TTATTGTGTT ATAATAAATA GAAGTACA               1198
```

( 2 ) INFORMATION FOR SEQ ID NO:4:

( i ) SEQUENCE CHARACTERISTICS:
( A ) LENGTH: 18
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: No ( i x ) FEATURE:
( A ) NAME/KEY:
( B ) LOCATION:
( C ) IDENTIFICATION METHOD:
( D ) OTHER INFORMATION: Primer from the flanking sequence of 5'to gene 1 of p39 in B. burgdorferi.

( x i ) SEQUENCE DESCRIPTION: SEQ ID NO:4:

```
ATGAATAAAA TATTGTTG                                       18
```

( 2 ) INFORMATION FOR SEQ ID NO:5:

( i ) SEQUENCE CHARACTERISTICS:
( A ) LENGTH: 18
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: No -continued ( i x ) FEATURE:
( A ) NAME/KEY:
( B ) LOCATION:
( C ) IDENTIFICATION METHOD:
( D ) OTHER INFORMATION: A primer from within the insertion sequence of genes 1 and 2 of p39 in B. burgdorferi.

( x i ) SEQUENCE DESCRIPTION: SEQ ID NO:5:

AATAAATTCT TTAAGAAA 18

( 2 ) INFORMATION FOR SEQ ID NO:6:

( i ) SEQUENCE CHARACTERISTICS:
( A ) LENGTH: 18
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: No ( i x ) FEATURE:
( A ) NAME/KEY:
( B ) LOCATION:
( C ) IDENTIFICATION METHOD:
( D ) OTHER INFORMATION: A primer from within the insertion sequence of genes 1 and 2 of p39 in B. burgdorferi.

( x i ) SEQUENCE DESCRIPTION: SEQ ID NO:6:

ATGAGAATTG TAATTTTT 18

( 2 ) INFORMATION FOR SEQ ID NO:7:

( i ) SEQUENCE CHARACTERISTICS:
( A ) LENGTH: 18
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: No ( i x ) FEATURE:
( A ) NAME/KEY:
( B ) LOCATION:
( C ) IDENTIFICATION METHOD:
( D ) OTHER INFORMATION: A primer from within the insertion sequence of 5'to gene 2 of p39 in B. burgdorferi.

( x i ) SEQUENCE DESCRIPTION: SEQ ID NO:7:

TAAATTTAAT ATTTGTTT 18

ANTIGENIC PROTEINS OF BORRELIA BURGDORFERI

This is a continuation of application Ser. No. 07/664,731, filed on Mar. 5, 1991, now abandoned, which is a continuation-in-part of U.S. Ser. No. 07/487,716, filed on Mar. 5, 1990, now abandoned.

FIELD OF THE INVENTION

The present invention relates to antigenic *Borrelia burgdorferi* proteins and their encoding DNA. In particular, the present invention relates to two 39 kilodalton (kDa) Borrelia burgdorferi proteins which react with Lyme borreliosis serum and a 28 kDa Borrelia burgdorferi protein which reacts with Lyme borreliosis serum.

BACKGROUND INFORMATION

Lyme borreliosis in humans is a multisystemic disorder caused by infection with the tick-borne spirochete, *Borrelia burgdorferi,* (Burgdorfer et al. 1982. Science 216:1317–1319; Johnson et al. 1984. Int. J. Syst. Bacteriol. 34:496–497; and Steere et al. 1983. N. Engl. J. Med. 308:733–740). Since the first epidemiological investigations of this disease in south-central Connecticut (Steere et al. 1977. Ann. Intern. Med. 86:685–698 and Steere et al. 1977. Arthritis. Rheum. 20:7–17), human cases of Lyme borreliosis have now been acquired in 43 states of the United States (Centers for Disease Control 1989, Lyme Disease—United States, 1987 and 1988. MMWR 38:668–672), five provinces of Canada, (Centers for Disease Control 1989, Lyme disease—Canada. MMWR 38:677–678), numerous countries throughout Europe and Asia (Ai et al. 1988. Ann. N.Y. Acad. Sci. 539:302–313; Dekonenko et al. 1988. J. Infect. Dis. 158:748–753; and Schmid. 1985. Rev. Infect. Dis. 7:41–50), and possibly restricted foci in Australia (Stewart et al. 1982. Med. J. Australia 1:139) and Africa (Haberberger et al. 1989. Trans. R. Soc. Trop. Med. Hyg. 83:556 and Stanek et al. 1986. Zentralbl. Bakteriol. Mikrobio. Hyg. [A] 263:491–495). Between 1982–1988, reports of 13,825 cases of Lyme borreliosis were received by the Centers for Disease Control from all 50 states of the United States, (Centers for Disease Control 1989, Lyme Disease—United States, 1987 and 1988. MMWR 38:668–672), making this disease the most prevalent arthropod-borne infection in the country.

With the dramatic increase in awareness, prevalence, and geographical distribution of Lyme borreliosis, a tremendous new demand has been placed on clinical laboratories for serological confirmation of cases, (Magnarelli. 1989. J. Am. Med. Assoc. 262:3464–3465 and Schwartz et al. 1989. J. Am. Med. Assoc. 262:3431–3434) or to rule out this disease in differential diagnoses. However, many potential problems exist with the currently available serological tests for Lyme borreliosis, which may result in either false positive or false negative results (Magnarelli 1989. J. Am. Med. Assoc. 262:3464–3465). Some studies have focused on using flagellar protein of *B. burgdorferi* to increase the sensitivity of serological tests (Hansen et al. 1989. J. Clin. Microbiol 27:545–551 and Hansen et al. 1988. J. Clin. Microbiol 26:338–346) because earlier studies demonstrated that it appeared to be the 41 kilodalton (kDa) flagellar subunit (flagellin) of the spirochete that generated the earliest antibody response in infected humans (Barbour et al. 1983. J. Clin. Invest. 72:504–515; Coleman et al. 1987. J. Infect. Dis. 155:756–765; and Grodzicki et al. 1988. J. Infect. Dis. 157:790–797). One of two potential problems with using flagellar protein, however, is that flagella of other Borrelia species share epitopes common to the flagella of *B. burgdorferi* (Barbour et al. 1986. Infect. Immun. 52:549–544). Secondly, in most studies that have screened human sera by immunoblot analysis (Barbour. 1984. Yale J. Biol. Med. 57:581–586; Barbour et al. 1983. J. Clin. Invest. 72:504–515; Coleman et al. 1987. J. Infect. Dis. 155:756–765; Craft et al. 1986. J. Clin. Invest. 78:934–939; and Nadal et al. 1989. Pediatr. Res. 26:377–382), antibodies binding the protein with an apparent migration of 41 kDa have been assumed, but not proven, to be flagellin.

Thus, it is clear that a need exists for a method of detecting Lyme borreliosis disease in mammals. The present invention provides such a method.

SUMMARY OF THE INVENTION

It is an object of the present invention to provide a means for detecting mammals previously or presently infected with Lyme disease.

In one embodiment, the present invention relates to substantially pure forms of a *Borrelia burgdorferi* proteins which have molecular weights of about 39 kilodaltons and a protein which has a molecular weight of about 28 kilodaltons as determined by SDS-PAGE and which are reactive with Lyme borreliosis serum.

In another embodiment, the present invention relates to *Borrelia burgdorferi* proteins substantially free of proteins with which they are normally associated that have molecular weights of about 39 kilodaltons and a protein which has a molecular weight of about 28 kilodaltons as determined by SDS-PAGE and which are reactive with Lyme borreliosis serum.

In yet another embodiment, the present invention relates to a DNA fragment encoding all, or a unique portion, of the above described 39 kilodalton *Borrelia burgdorferi* proteins or the 28 kilodalton *Borrelia burgdorferi* protein.

In another embodiment, the present invention relates to a DNA fragment encoding all, or a unique portion, of one of the above described 39 kilodalton *Borrelia burgdorferi* proteins.

In a further embodiment, the present invention relates to a recombinant DNA molecule comprising a fragment of the above described DNA and a vector. The invention also relates to a host cell stably transformed with such a recombinant DNA molecule in a manner allowing expression of the *Borrelia burgdorferi* proteins encoded in the DNA fragment.

In another embodiment, the present invention relates to a method of producing recombinant *Borrelia burgdorferi* proteins of about 39 kilodaltons and a protein of about 28 kilodaltons and which are reactive with Lyme borreliosis serum which method comprises culturing host cells expressing the proteins, in a manner allowing expression of the proteins, and isolating the proteins from the host cells.

In a further embodiment, the present invention relates to a purified form of an antibody specific for the above described 39 kilodalton *Borrelia burgdorferi* proteins or a unique fragment thereof or the above described 28 kilodalton *Borrelia burgdorferi* protein or a unique fragment thereof.

In another embodiment, the present invention relates to a vaccine for mammals against Lyme disease comprising all, or a unique portion, of the above described 39 kilodalton *Borrelia burgdorferi* proteins, each of the 39 kDa proteins or the above described 28 kilodalton protein *Borrelia burgdorferi* protein which are reactive with Lyme borreliosis serum, in an amount sufficient to induce immunization against Lyme disease, and a pharmaceutically acceptable carrier.

In a further embodiment, the present invention relates to a bioassay for the diagnosis of Lyme borreliosis disease comprising the steps of coating a surface with the 39 kDa proteins, each of the 39 kDa proteins or the 28 kDa protein of this invention (or antibodies specific therefor), contacting the surface with serum and detecting the presence or absence of a complex formed between the coated proteins (or coated antibodies) and antibodies specific therefor (or the target protein) in the serum.

In another embodiment, the present invention relates to a diagnostic kit comprising natural or recombinantly produced *Borrelia burgdorferi* 39 kDa proteins, each of the 39 kDa proteins or a 28 kDa protein and ancillary reagents suitable for use in detecting the presence of antibodies to the protein in a mammalian tissue sample.

In yet another embodiment, the present invention relates to a method of screening drugs for anti-Lyme borreliosis disease activity comprising contacting the drug with cells contacted with *Borrelia burgdorferi* under conditions such that inhibition of anti-Lyme activity can be effected.

Various other objects and advantages of the present invention will become obvious from the drawings and the following description of the invention.

All publications mentioned herein are hereby incorporated by reference.

Figure 1:
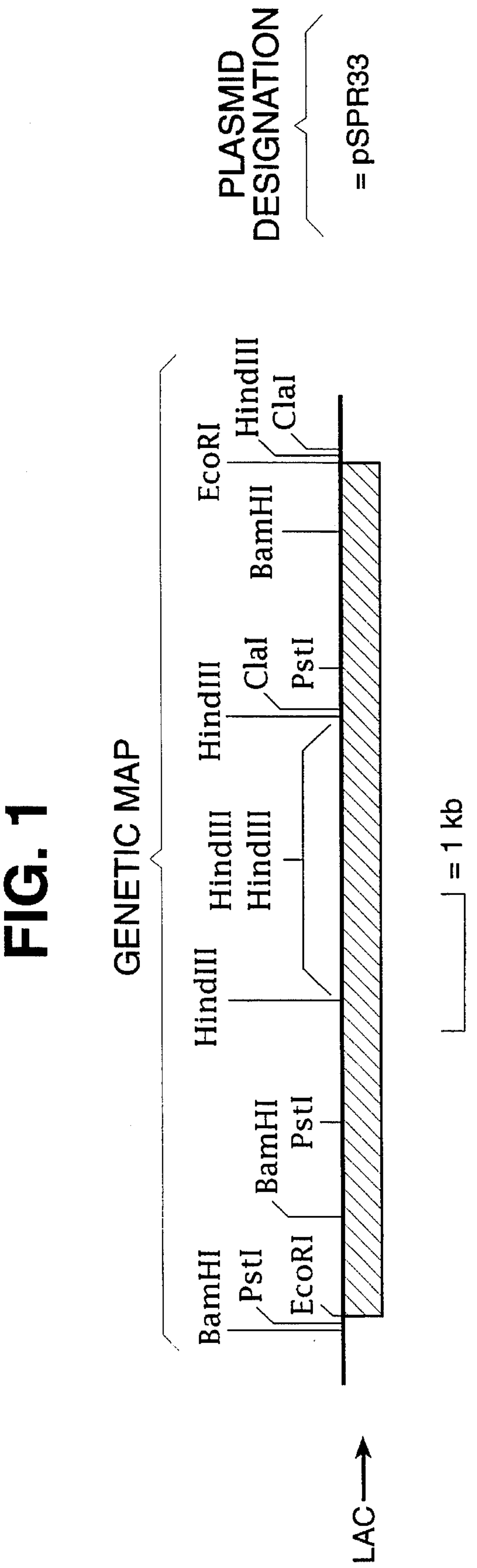
FIG. 1 shows a genetic map of pSPR33. Spirochete DNA is denoted as a striped block and the arrow indicates the direction that the Lac promoter is transcribed. There were no restriction sites within the spirochete EcoRI fragment for AccI, KpnI, XbaI, XhoI or SmaI.

*B. burgdorferi* strains (including low (P6) (lane 3) and high (P246) (lane 12) in vitro passages of strain Sh-2-82) and isolates representing 5 additional Borrelia species were immunoblotted with anti-pSPR33 serum. Lysates of E. coli that express P28 and P39 (E. coli+pSPR33) (lane 1) and that do not (E. coli+vector) (lane 2) were also immunoblotted as positive and negative controls respectively. Lane 4 is CT20004; land 5 is NY-13-87; lane 6 is TX1352; lane 7 is CT22921; lane 8 is CT27985; lane 9 is CA-2-87; lane 10 is CT26816; lane 11 is ECM-NY-86; lane 13 is *B. hermsii*; lane 14 is *B. parkeri*; lane 15 is *B. anserina;* lane 16 is *B. turicatae;* and lane 17 is *B. coriacea.* Not all of the 20 *B. burgdorferi* isolates tested are shown (see Table 1).

Figure 6:
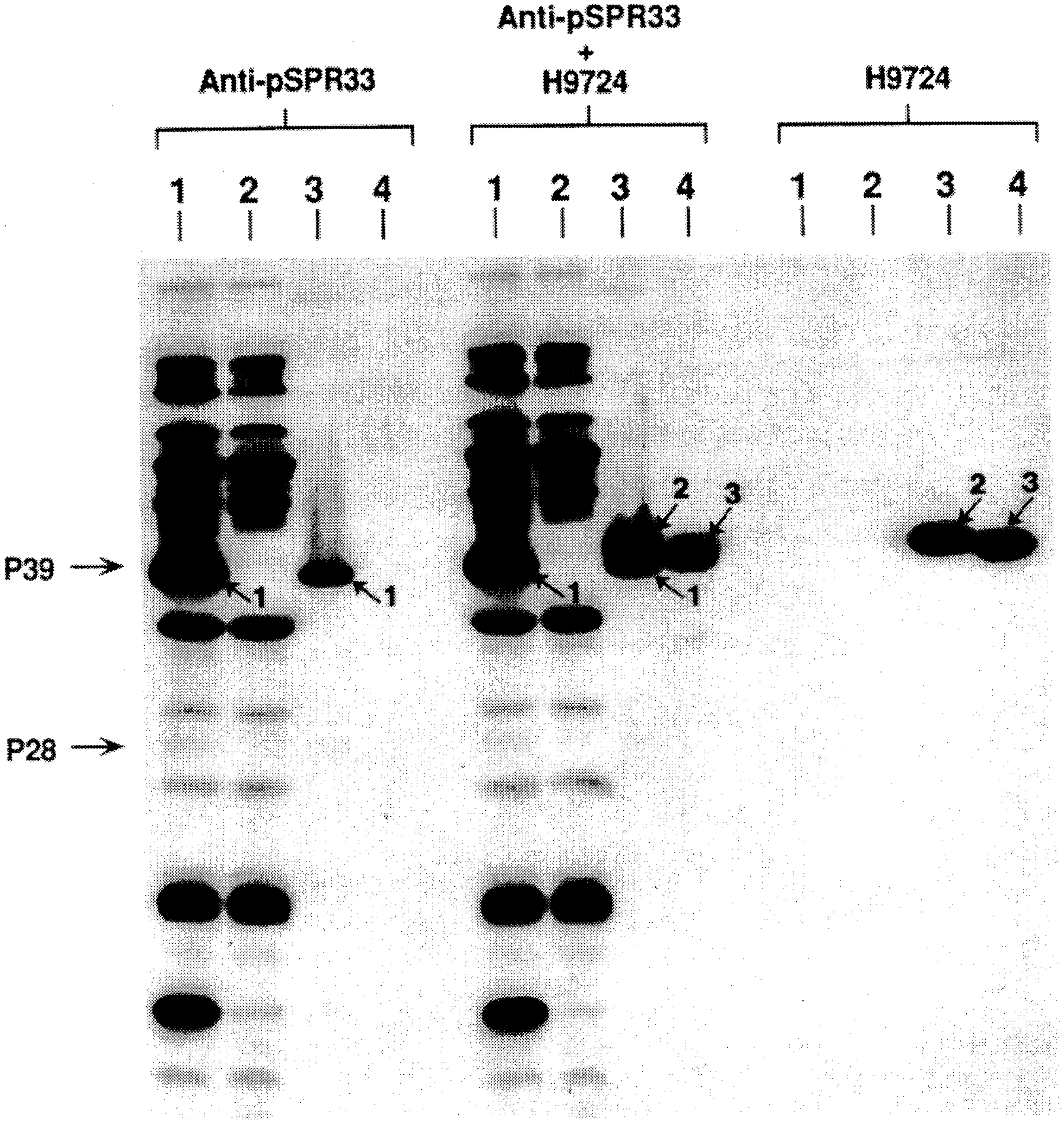

FIG. 6 comprises the reactivity of anti-pSPR33 and monoclonal antibody H9724. Components in whole cell lysates of E. coli plus pSPR33, (lanes 1) E. coli plus vector only (lane 2), *B. burgdorferi* strain Sh-2-82 (lanes 3) and *B. hermsii* strain FRG (lane 4) were separated by SDS-PAGE and were incubated with anti-pSPR33, anti-pSPR33 plus H9724, or H9724. P39 (arrow 1); 41 kDa flagellin from B. burgdorferi (arrow 2); 39 kDa flagellin from *B. hermsii* (arrow 3).

Figure 7A:
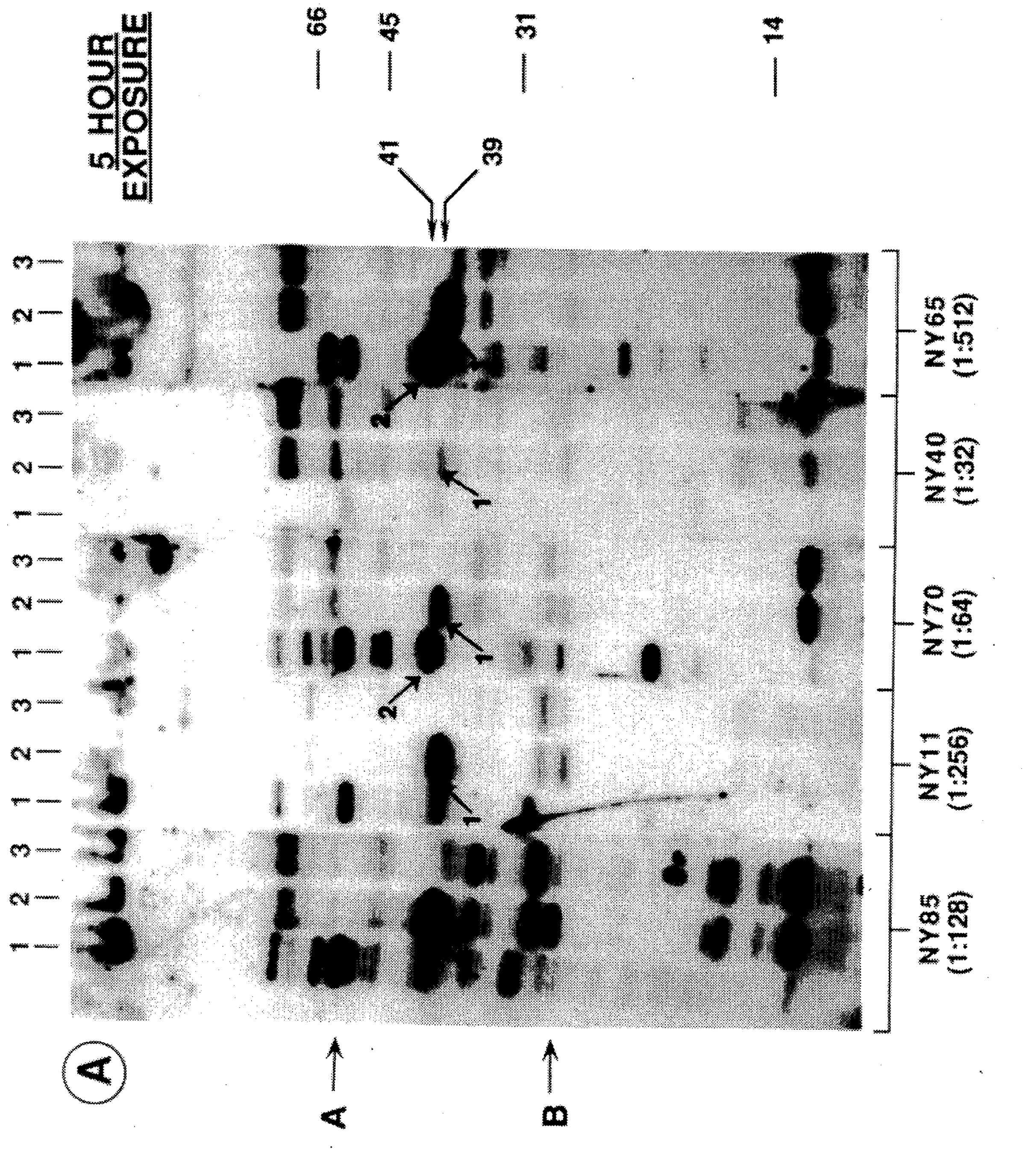
Figure 7B:
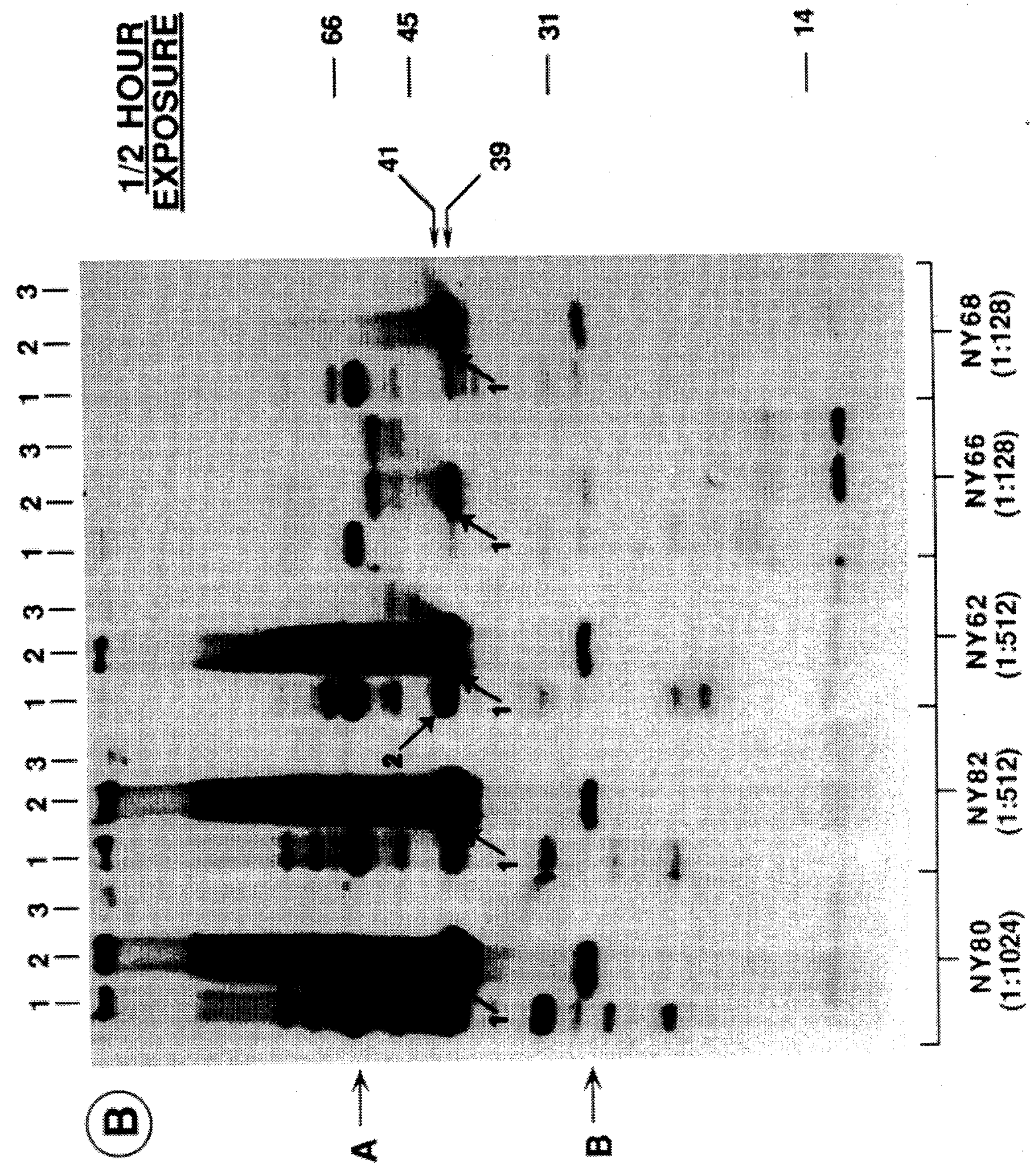

FIGS. 7A and 7B show immunoblot analysis of 10 human Lyme borreliosis sera and their reactivity with P28 and P39. Whole-cell lysates of *B. burgdorferi* strain Sh-2-82 (lane 1), E. coli carrying pSPR33 (lane 2) and E. coli carrying only vector (lane 3) were immunoblotted with human Lyme borreliosis sera (NY). IFA Lyme borreliosis titers for each human serum are indicated below their designations. Autoradiographs exposed for 5 hr. (panel A) represented sera having weaker reactivity than those exposed for ½ hr. (panel B). Arrows denote P39 (arrow 1) and a 41 kDa antigen (arrow 2). Band B corresponds to the position of P28 and band A is an 58–65 kDa antigen that bound all sera that reacted with P39. Molecular mass markers (kDa) are indicated on the right of each panel.

Figure 8:
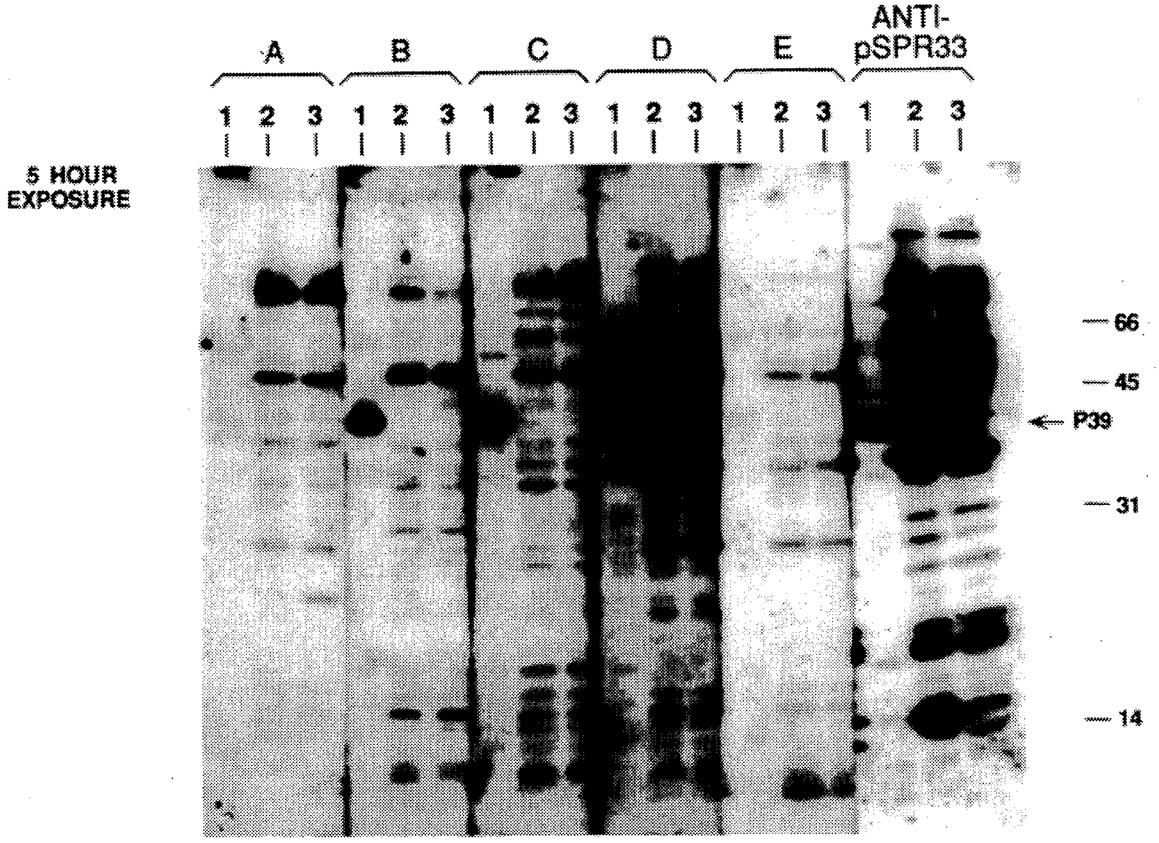

FIG. 8 shows immunoblot analysis of syphilitic sera. Whole-cell lysates of *B. burgdorferi* strain Sh-2-82 (lanes 1), E. coli carrying pSPR33 (lane 2) and E. coli carrying only (lanes 3) vector were immunoblotted with 5 syphilitic sera (1 to 5) or anti-pSPR33 (anti-pSPR33). Molecular mass markers are indicated on the right. Note absence of P39 in pSPR33 lanes reacted with syphilitic sera which contrasts with a strongly reactive 41 kDa antigen in three of the five *B. burgdorferi* lanes.

Figure 9:
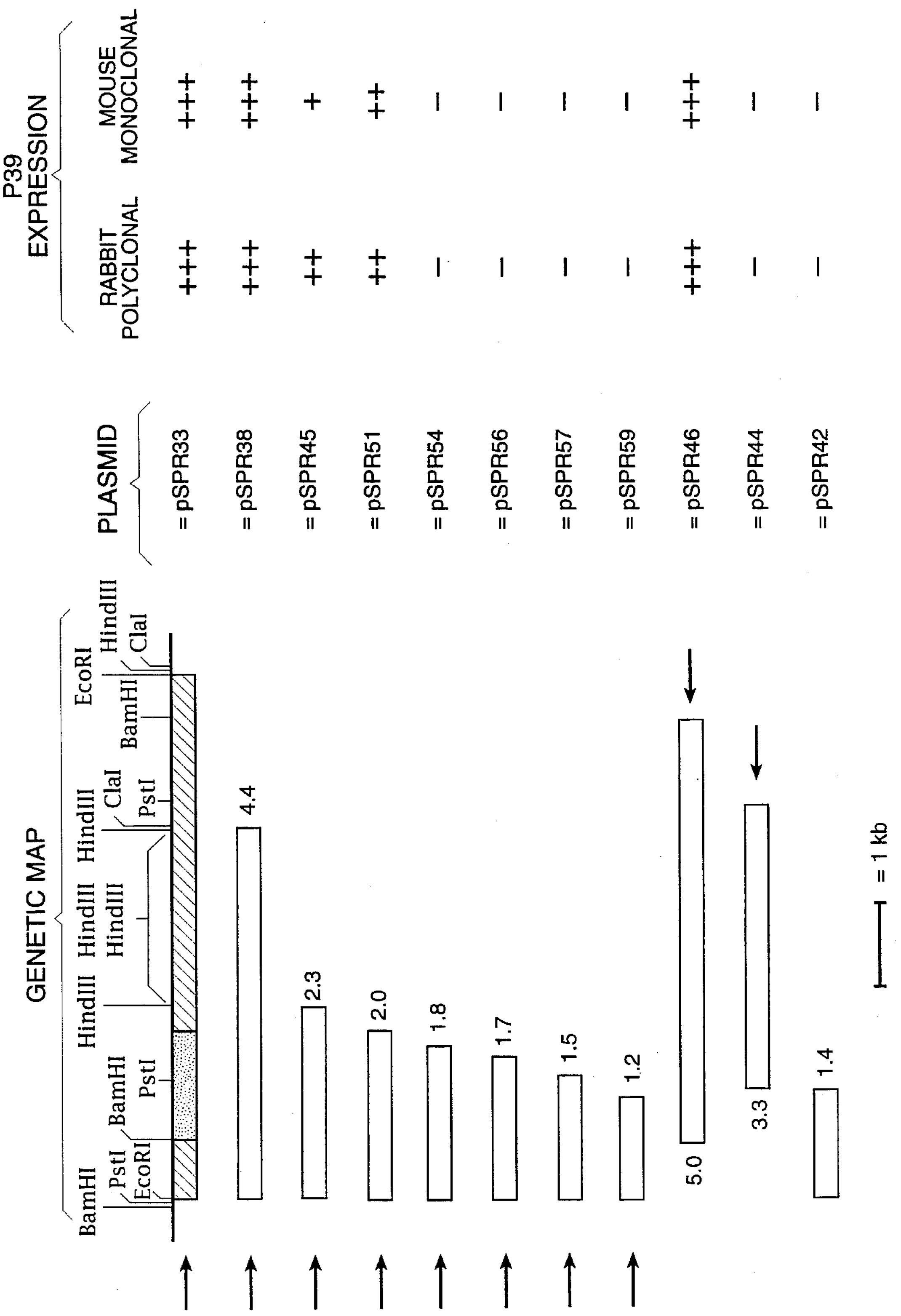

FIG. 9 shows a restriction endonuclease map and expression data for the P39 locus of *Borrelia burgdorferi.* Subclones and deletion variants of plasmid pSPR33 (pSPR38, pSPR45, pSPR51, pSPR54, pSPR56, pSPR57, pSPR59, pSPR38, pSPR45, pSPR51, pSPR54, pSPR56, pSPR57, pSPR59, pSPR46, pSPR44 and pSPR42) are indicated as open bars.

Figure 10A:
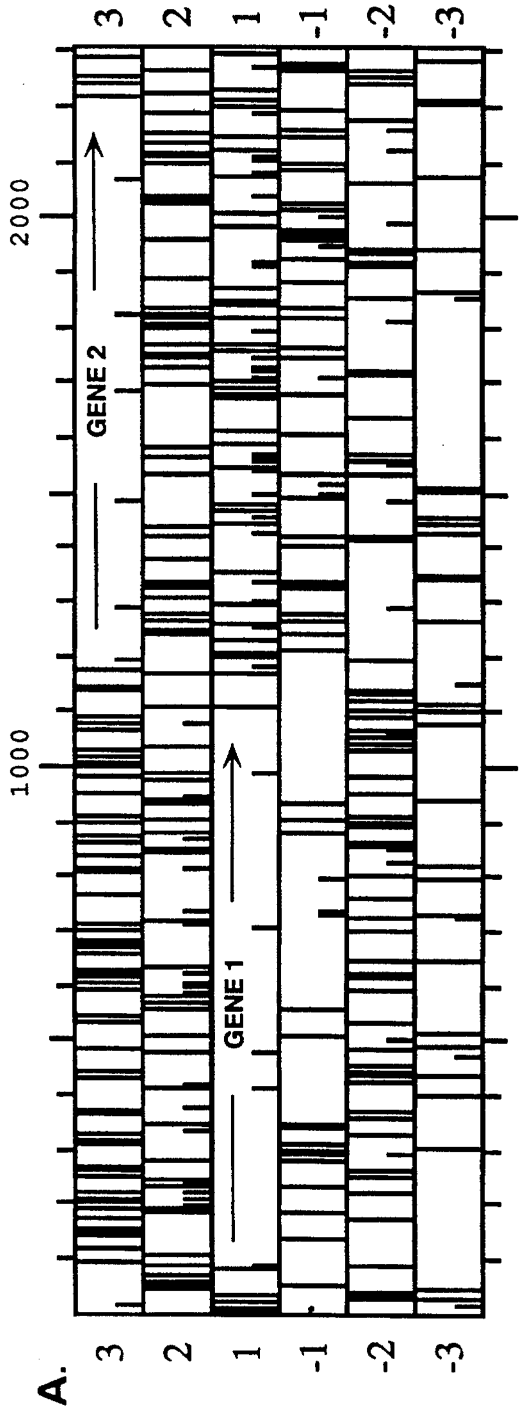
Figure 10B:
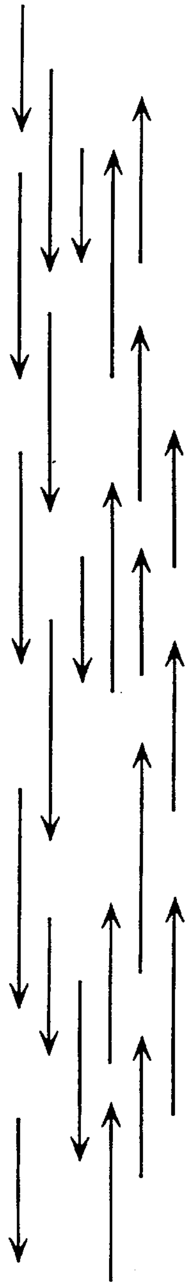

FIGS. 10A and 10B show a map of the open reading frames of gene-1 and gene 2 encoding the P39 α and P39 β antigens, respectively, of *Borrelia burgdorferi.* FIG. 10*a* shows the frames clear of termination sites (complete vertical lines). FIG. 10*b* shows primer sites with overlapping sequences used to determine nucleotide sequences of both strands of DNA.

Figures 11, 13:
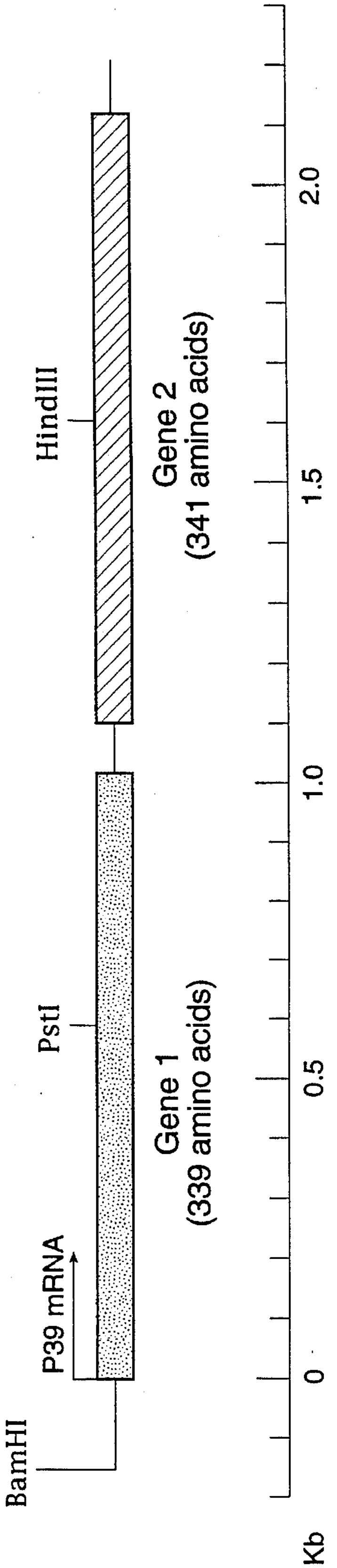

FIG. 11 shows a genetic map of the P39 operon of *Borrelia burgdorferi* including the position of genes 1 and 2, the number of deduced amino acid, and the direction of transcription.

Figure 12:
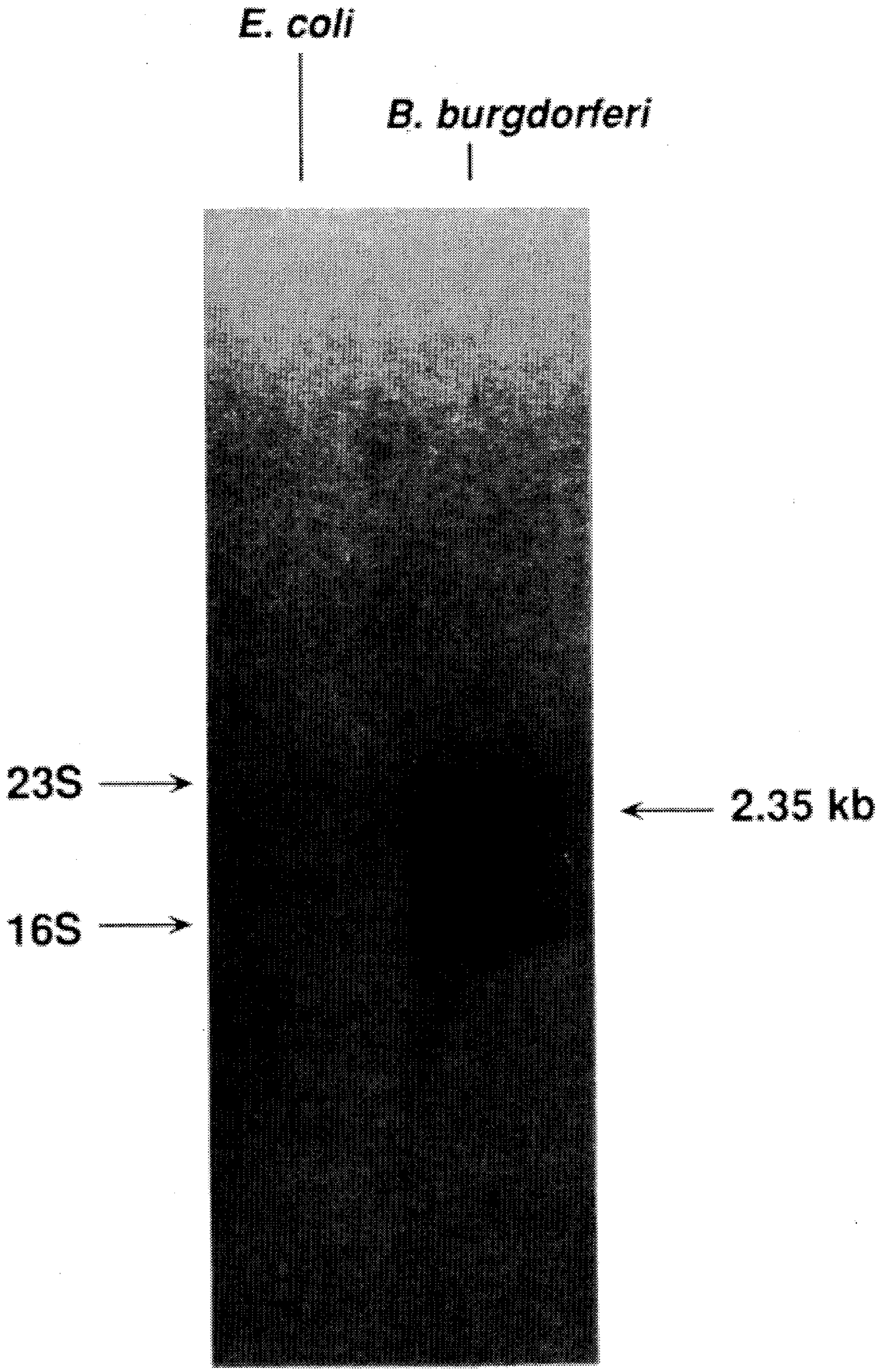

FIG. 12 shows northern blot of *Borrelia burgdorferi* RNA probed with pSPR33 showing a 2.35 kb RNA transcript of the appropriate size for the single transcriptional unit for genes 1 and 2.

FIG. 13 shows the deduced amino-terminal ends of P39 α (gene 1) and P39 β (gene 2), and the major outer surface proteins (Osp) A and B of *Borrelia burgdorferi.*

Figure 14A:
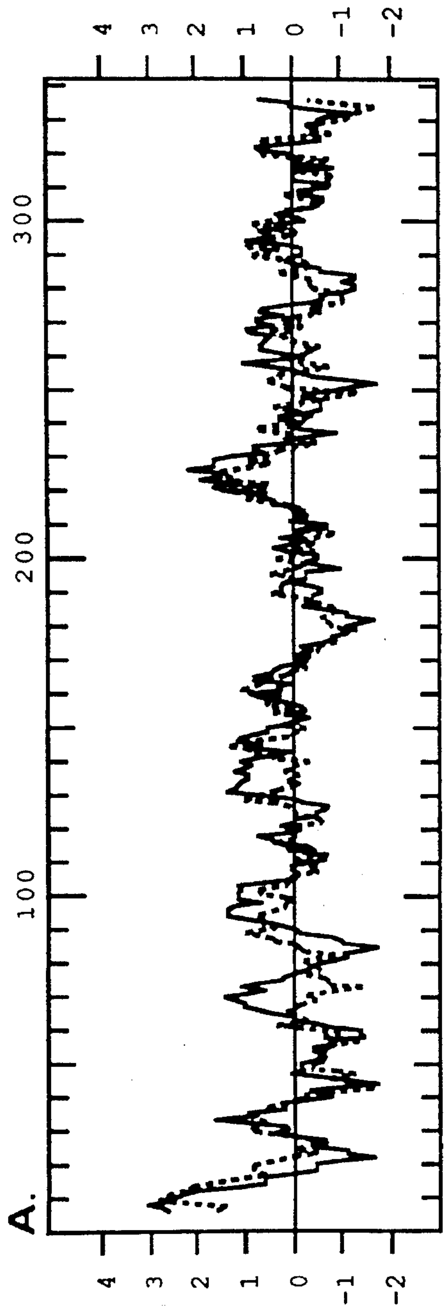
Figure 14B:
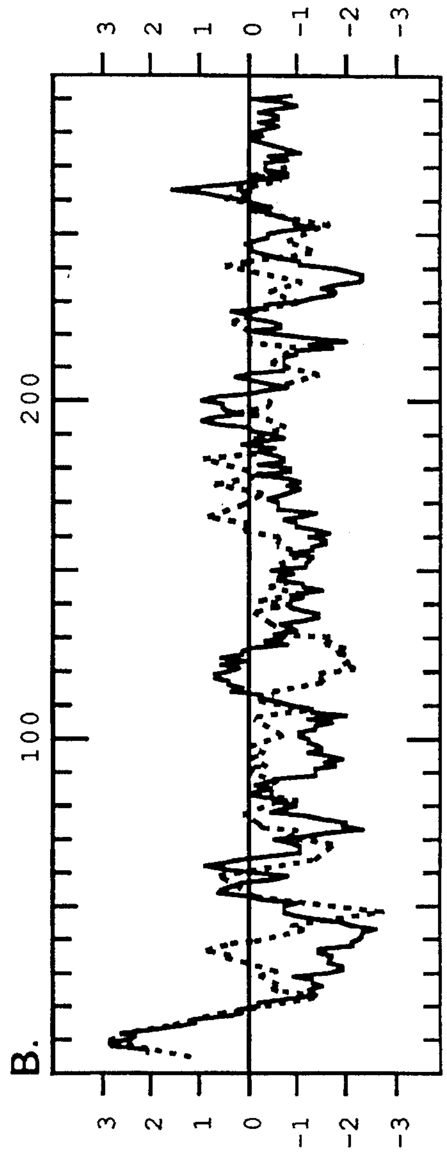

FIG. 14A and 14B show hydrophobicity plots of the deduced amino acid sequences of P39 α (dotted line) and P39 β (solid line) (Panel A) and OspA (dotted line) and OspB (solid line) (Panel B) of Borrelia burgdorferi (+ values show hydrophilic regions and–values show hydrophobic regions of the proteins).

DETAILED DESCRIPTION OF THE INVENTION

This invention relates, in part, to *Borrelia burgdorferi* antigenic proteins and their encoding DNA. A principle embodiment of this aspect of the present invention relates to three antigenic *Borrelia burgdorferi* proteins. Two proteins are characterized by a molecular weight of about 39 kDa (designated 39α and 39β) as determined by SDS-PAGE and reactivity with human Lyme borreliosis serum. The third protein is characterized by a molecular weight of about 28 kDa as determined by SDS-PAGE and reactivity with human Lyme borreliosis serum. The present invention also relates to unique portions of the above proteins wherein a unique portion consists of at least 5 (or 6) amino acids.

The 39 kDa and 28 kDa proteins are substantially free of proteins with which they are normally associated. A substantially pure form of the proteins of the present invention can be obtained by one skilled in the art using standard methodologies for protein purification without undue experimentation. The present invention also relates to peptide fragments of the 39 kDa or 28 kDa protein. Alternatively, the proteins and peptides of the invention can be chemically synthesized using known methods.

The present invention also relates to a DNA fragment encoding all, or a unique portion, of the 39 kDa *B. burgdorferi* proteins or the 28 kDa *B. burgdorferi* protein of the present invention. A principle embodiment of this aspect of the invention relates to the 6.3 kilobase pair EcoRI fragment obtained from a DNA library of *B. burgdorferi* DNA which encodes the 39 kDa and 28 kDa antigenic proteins.

The present invention also relates to a DNA fragment encoding all, or a unique portion, of the 39 kDa α *B. burgdorferi* protein or the 39 kDa β *B. burgdorferi* protein.

The present invention further relates to a recombinant DNA molecule and to a host cell transformed therewith. Using standard methodology well known in the art, a recombinant DNA molecule comprising a vector and a DNA fragment encoding both the 39 kDa proteins of this invention, either of the 39 kDa proteins or the 28 kDa protein can be constructed using methods known in the art without undue experimentation. The DNA fragment can be isolated from *B. burgdorferi,* and it can take the form of a cDNA clone produced using methods well known to those skilled in the art or it can be produced by polymerase chain reaction. Possible vectors for use in the present invention include, but are not limited to, λZAPII, pUC8 or preferably high frequency expression vectors such as pBluescript II SK, pNH8a. The host cell can be prokaryotic (such as bacterial), lower eukaryotic (such as fungal, including yeast) or higher eukaryotic (such as mammalian).

The present invention further relates to antibodies specific for the 39 kDa *B. burgdorferi* proteins or the 28 kDa protein of the present invention. One skilled in the art using standard methodology can raise monoclonal antibodies and polyclonal antibodies to the 39 kDa proteins or the 28 kDa protein, or a unique portion thereof. This is exemplified by the anti-pSPR33 rabbit antiserum (see Example 2 below).

The present invention also relates to a vaccine for use in mammals against Lyme borreliosis disease. In one embodiment of this aspect of this invention, as is customary for vaccines, the 39 kDa proteins, either of the 39 kDa proteins or the 28 kDa protein of the present invention can be delivered to a mammal in a pharmacologically acceptable vehicle. As one skilled in the art will understand, it is not necessary to use the entire protein. A unique portion of the protein (for example, a synthetic polypeptide corresponding to a portion of the 39 or 28 kDa proteins) can be used. Vaccines of the present invention can include effective amounts of immunological adjuvants known to enhance an immune response. The protein or polypeptide is present in the vaccine in an amount sufficient to induce an immune response against the antigenic protein and thus to protect against Lyme borreliosis infection. Protective antibodies are usually best elicited by a series of 2–3 doses given about 2 to 3 weeks apart. The series can be repeated when circulating antibodies concentration in the patient drops.

The present invention further relates to diagnostic assays for use in human and veterinary medicine. For diagnosis of Lyme borreliosis disease, the presence of antibodies to the 39 kDa proteins or the presence of the 28 kDa proteins in mammalian serum is determined. Many types of tests, as one skilled in the art will recognized, can be used for detection. Such tests include, but are not limited to, IFA, RIA, RIST, ELISA, agglulination and hemagglutination. The diagnostic assays can be performed using standard protocols such as those described by Magnarelli et al. 1984. J. Clin. Microbiol. 20:181–184; Craft et al. 1984. J. Infect. Dis. 149:789–795; Engvall et al. 1971. Immunochemistry 8:871–874; and Russell et al. 1984. J. Infect. Dis. 149:465–470.

Specifically, a diagnostic assay of the present invention can be constructed by coating on a surface (i.e. a solid support) for example, a microtitration plate or a membrane (e.g. nitrocellulose membrane), all or a unique portion of the 39 kDa proteins (natural or synthetic), either of the 39 kDa proteins (natural or synthetic) or the 28 kDa protein (natural or synthetic) and contacting with the serum from a patient suspected of having Lyme borreliosis disease. The presence of a resulting complex formed between the surface and antibodies specific therefore in the serum can be detected by any of the known methods common in art, such as fluorescent antibody spectroscopy or colorimetry.

In another embodiment of the diagnostic assay of the present invention, all or a unique portion of the 39 kDa proteins, either of the 39 kDa proteins or the 28 kDa protein is bound to an inert particle of, for example, bentonite or polystyrene latex. The particles are mixed with serum from a patient in, for example, a well of a plastic agglutination tray. The presence or absence of antibodies in the patient's serum is determined by observing the settling pattern of the particles in the well.

In a further embodiment of the diagnostic assay of the present invention, the presence or absence of the 39 kDa proteins, or the 28 kDa protein in a serum sample is detected. Antibodies specific for the 39 kDa proteins, either of the 39 kDa proteins or the 28 kDa protein or a unique portion thereof can be coated on to a solid surface such as a plastic and contacted with the serum sample. After washing, the presence or absence of the protein from the serum bound to the fixed antibodies is detected by addition of a labeled (e.g. fluorescently labeled) antibody specific for the 39 (or 28)

kDa proteins.

One skilled in the art will appreciate that the invention includes the use of competition type assays in detecting in a sample the antigens and antibodies to which this invention relates.

The present invention further relates to screening for anti-Lyme borreliosis disease drugs. In one embodiment potential anti-Lyme borreliosis disease drugs are tested for their ability to inhibit expression of the 39 kDa proteins or the 28 kDa protein in cells contacted with the *B. burgdorferi.* The presence or absence of the 39 kDa proteins or 28 kDa protein in exposed cells treated with test drugs can be determined by any of the standard diagnostic assays mentioned above.

The present invention further relates to DNA fragments containing the nucleotide sequence as shown in SEQ. ID. Nos. 1–3, or mutants thereof, to recombinant molecules containing the DNA fragments and host cells transformed with the recombinant molecules. Using standard methodology well known in the art, a recombinant DNA molecule comprising a vector and the DNA fragments of this invention can be constructed using methods known in the art without undue experimentation. The DNA fragments can be isolated from *B. burgdorferi* or can be produced by a polymerase chain reaction. Possible vectors for use in the present invention include but are not limited to, pUC, pBluescript or pBR322. The host cell can be prokaryotic (such as bacterial), lower eukaryotic (such as fungal, including yeast) or higher eukaryotic (such as mammalian).

The present invention further relates to methods of producing recombinant *Borrelia burgdorferi* 39 kDa and 28 kDa proteins comprising culturing the aforementioned host cells in a manner allowing expression of the proteins and isolating the proteins from the host cells. Methodology utilize to produce recombinant *B. burgdorferi* proteins are well within the skill of an ordinary artisan.

EXAMPLES

The following organisms and materials were used throughout the Examples.

Bacterial strains. *B. burgdorferi* strains used (See Table 1 below) have been previously described or were kindly provided by Dr. John Anderson (Connecticut Agriculture Experiment Station, New Haven, Conn.), Dr. Alan MacDonald (Southampton Hospital, Long Island, N.Y.), and Ms. Glenna Teltow and Ms. Julie Rawlings (Medical Entomology Section, Bureau of Laboratories, Texas Department of Health, Austin., Tex.). The five strains representing *B. hermsii* (HS1), *B. coriaceae* (Co53), *B. parkeri, B. turicatae* and *B. anserina* have been described previously (Schwan et al. 1989. J. Clin. Microbiol. 27:1734–1738). Borrelia organisms were cultured at 32° C. in BSK-II medium as previously described (Barbour. 1984. Yale J. Biol. Med. 57:581–586).

TABLE 1

Summary of *Borrelia burgdorferi* strains used in this study all of which expressed P28 and P39.

| Strain designation | In vitro° passages (H)igh/(L)ow | Biological* source | Geographical* source (year isolated) | Obtained from (reference) |
|---|---|---|---|---|
| Sh-2-82 (P6) | L | Id | New York (1982) | Schwan et al. (1) |
| Sh-2-82 (P246) | H | Id | New York (1982) | Schwan et al. (1) |
| B31 | H | Id | New York (1982) | Schwan et al. (1) |
| CA-2-87 | L | Ip | California (1987) | Schwan et al. (1) |
| CA-3-87 | L | Ip | California (1987) | Schwan et al. (1) |
| NY-1-86 | L | H | New York (1986) | Schwan et al. (1) |
| ECM-NY-86 | L | H | New York (1986) | Schwan et al. (1) |
| NY-6-86 | L | H | New York (1982) | MacDonald |
| NY-13-86 | L | H | New York (1982) | MacDonald |
| CT20004 | L | Ir | France (1985) | Anderson |
| CT22921 | L | Rp | New York (1986) | Anderson |
| CT26816 | L | Rm | Rhode Island (1985) | Anderson |
| CT19678 | L | Rp | New York (1986) | Anderson |
| CT21343 | L | Rp | Wisconsin (1986) | Anderson |
| CT21305 | L | Rp | Connecticut (1986) | Anderson |
| CT21721 | L | Id | Wisconsin (1986) | Anderson |
| CT27985 | L | Id | Connecticut (1988) | Anderson |
| TX1352 | H | Aa | Texas (1989) | Rawlings |
| PE92 | H | D | Texas (1989) | Rawlings |
| BR4-3028 | H | H | Texas (1989) | Rawlings |

+Tick = *Ixodes dammini* (Id); tick = *I. pacificus* (Ip); tick = *I. ricinus* (Ir); tick = *Amblyomma americanum* (Aa); human (H); rodent = *Peromyscus leucopus* (Rp); rodent = Microtum (Rm); dog = (D).
°Strains passed for ≦10 passages (L); strains passed for ≧20 passages (H).

*USA state or country.
1 = Schwan et al. 1989. J. Clin. Microbiol. 27:1734,1738.

Human syphilitic sera were kindly provided by Dr. Wayne Hogefre and Ms. Jane Markley (Hillcrest Biologicals, Cypress, Calif.), amyotrophic lateral sclerosis (ALS) sera were provided by Dr. Jeffrey Smith (Mount Sinai Medical Center, ALS Clinic, New York, NY.) and Dr. Alan MacDonald (Southampton Hospital, Long Island, N.Y.), and relapsing fever sera were collected from patients from Oregon and Washington. Normal sera were obtained from staff and laboratory personnel at Rocky Mountain Laboratories. Human Lyme borreliosis sera were provided by Dr. Alan MacDonald and were collected from patients clinically diagnosed with Lyme borreliosis from Long Island, N.Y.

*Escherichia coli* carrying the plasmid pSPR33 (see below) were deposited on Feb. 28, 1990 at the American Type Culture Collection 12301 Parklawn Drive, Rockville, Md. 20852. The accession number of the organism is 68243. The deposits shall be viably maintaining, replacing it if it becomes non-viable, for the life of the patent, for a period of 30 years from the date of the deposit or for five years from the last date of request or sample of the deposit, whichever is longer and made available to the public upon issuance of a patent from this application, without restriction, and in accordance with the provisions of the law. The Commissioner of Patents and Trademarks, upon request shall have access to the deposit.

Example 1. Cloning and Genetic Analysis of Borrelia DNA

To identify *B. burgdorferi* proteins that induce an antibody response during the course of an infection, a DNA library of *B. burgdorferi* containing EcoRI fragments was constructed in *E. coli* with the x expression vector λZAPII.

Total DNA was purified from 500 ml stationary phase borrelial cultures by a modification as previously described (Barbour. 1988. J. Clin. Microbiol. 26:475–478). Cells were recovered by centrifugation, washed in 20 ml of PBS plus 5 mMMgCl$_3$ and resuspended in 2.4 ml TES (50 mM Tris, pH 8.0; 50 mM EDTA, 15% (w/v) sucrose). Lysozyme was added to a final concentration of 1 mg/ml and then the cell suspension was left on ice for 10 min. Cells were lysed by adding 3 ml TES plus 1% (v/v) sodium deoxycholate and gently mixed for 10 min. at room temperature. Proteinase K (1 mg) was then added and the sample was incubated at 37° C. for 1 hr. The DNA suspension was then extracted twice with 1 volume of phenolchloroform (1:1 (v/v)) and once with chloroform-isoamyl alcohol (24:1 (v/v)). The DNA was ethanol precipitated, washed twice with 70% ethanol and resuspended to a final concentration of 1 mg/ml in TE (10 mM Tris, pH 7.6; 1 mM EDTA).

Total DNA (1 μg) from *B. burgdorferi* strain Sh-2-82 was digested with EcoRI, ligated to the dephosphorylated arms of the expression vector λZAPII (Stratagene, La Jolla, Calif.) and packaged according to the manufacturer's directions.

The library was screened for Borrelia by immunoblot with a convalescent serum from a human Lyme borreliosis patient from Long Island, N.Y. (1:100) following absorption of plaque proteins to nitrocellulose filters (Maniatis et al. 1982. Molecular Cloning: A Laboratory Manual. Cold Spring Harbor Laboratory, Cold Spring Harbor, N.Y.). After blocking for 1 hr. at 25° C. in TSE-Tween (50 mM Tris, pH 7.4; 150 mM NaCl; 5 mM EDTA; 0.05% Tween 20), filters were incubated with serum diluted in TSE-Tween with gentle rocking at 25° C. for 1 hr. They were then washed for 1 hr. with four changes of TSE-Tween and the bound antibody was detected by incubating the filters with $^{125}$I-labeled protein A (500,000 cpm/ml) for 1 hr. with rocking. Each filter was then washed four times for 15 min. each with TSE-Tween, dried and autoradiographed with Kodak X-AR5 film.

Figure 2:
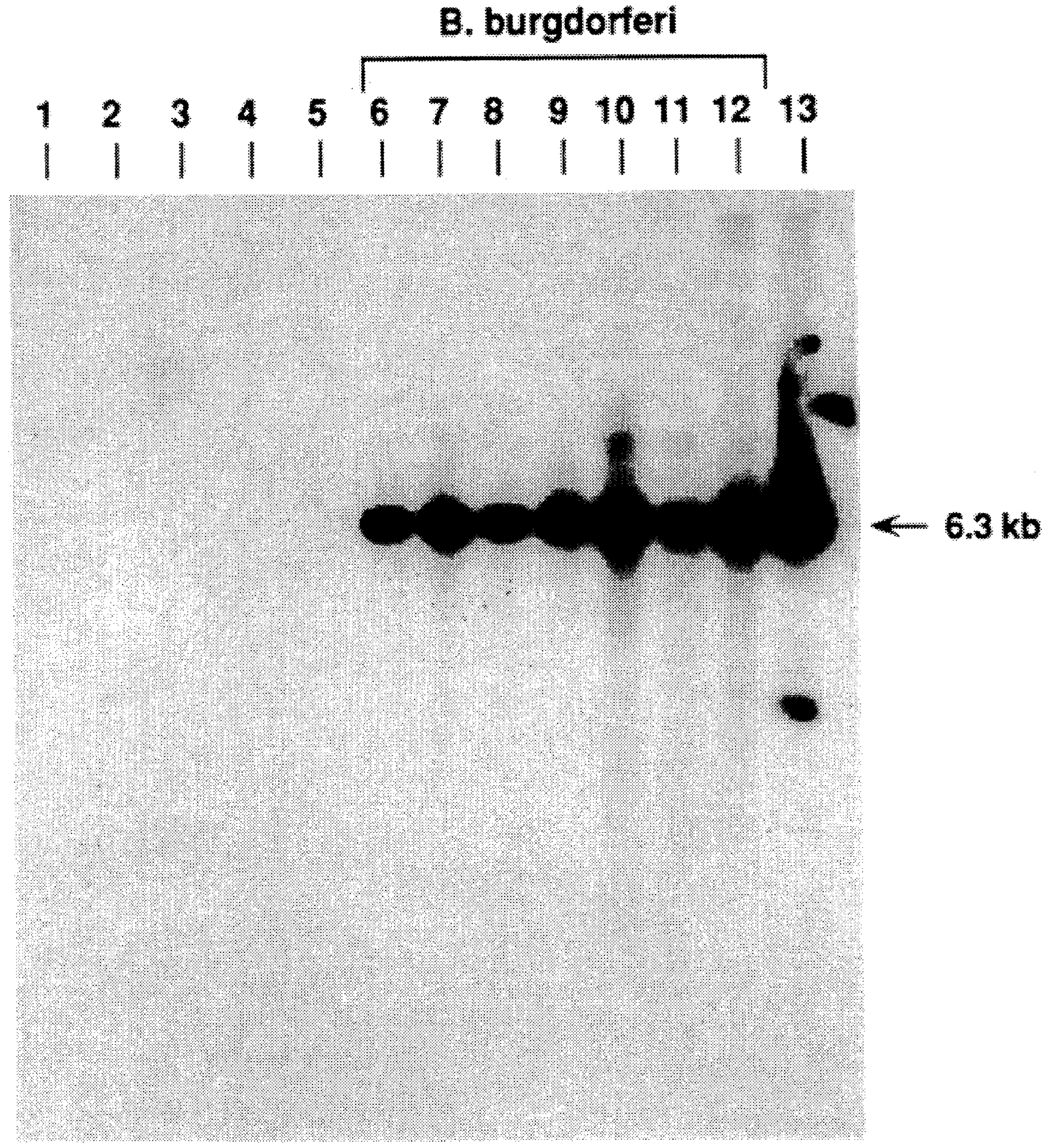
FIG. 2 is an autoradiograph showing hybridization of $^{32}$P-labeled insert DNA from pSPR33 with total DNA digested with EcoRI from 7 isolates of *B. burgdorferi* and 5 other Borrelia species. Lane 13 contained pSPR33 (pSPR33) digested with EcoRJ. Lane 1 is *B. hermsii*; lane 2 is *B. turicatae*; lane 3 is *B. coriaceae*; lane 4 is *B. anserina*; lane 5 is *B. parkeri*; lane 6 is CT26816; lane 7 is CT21343; lane 8 is CT27985; lane 9 is CT20004; lane 10 is CT21305; lane 11 is CA-3-87; and lane 12 is Sh-2-82. Linear molecular weight markers (Kb) are indicated on the right of the panel.

Positive clones were detected at a frequency of 5%. One recombinant plaque that reacted with human serum was plaque purified and the phagemid carrying the Borrelia DNA was excised from the x sequences with the aid of the helper phage R407 according to the suppliers directions (Stratagene). Excision of the cloned fragment from the purified phage produced the phagemid portion containing a 6.3 kilobase (Kb) EcoRI fragment, designated plasmid pSPR33 (FIG. 1). The fragment was isolated from an agarose gel, radiolabeled and shown to hybridize with a similar sized fragment in EcoRI digested total DNA from all six North American and one European *B. Burgdorferi* isolates (FIG. 2).

Recombinant plasmid pPSR33 was isolated from E. coli for mapping studies from 500 ml cultures and purified as previously described (Simpson et al. 1987. Infect. Immun. 55:2448–2455), except two consecutive dye-buoyant density gradients were preformed (Plasterk et al. 1985. Nature 318:257–263) in a Beckman VTi80 rotary at 70,000 rpm for 4 hr at 18° C. The supercoiled circular plasmid portion was diluted with two volumes of water after the removal of the ethidium bromide and then ethanol precipitated. The plasmid DNA was then resuspended in a minimal volume of TE. Mini-plasmid preparations (Maniatis et al. 1982. Molecular Cloning: A Laboratory Manual. Cold Spring Harbor Laboratory, Cold Spring Harbor, N.Y.) of positive clones were examined by agarose gel electrophoresis after their digestion with EcoRI to determine the insert size.

Figure 3B:
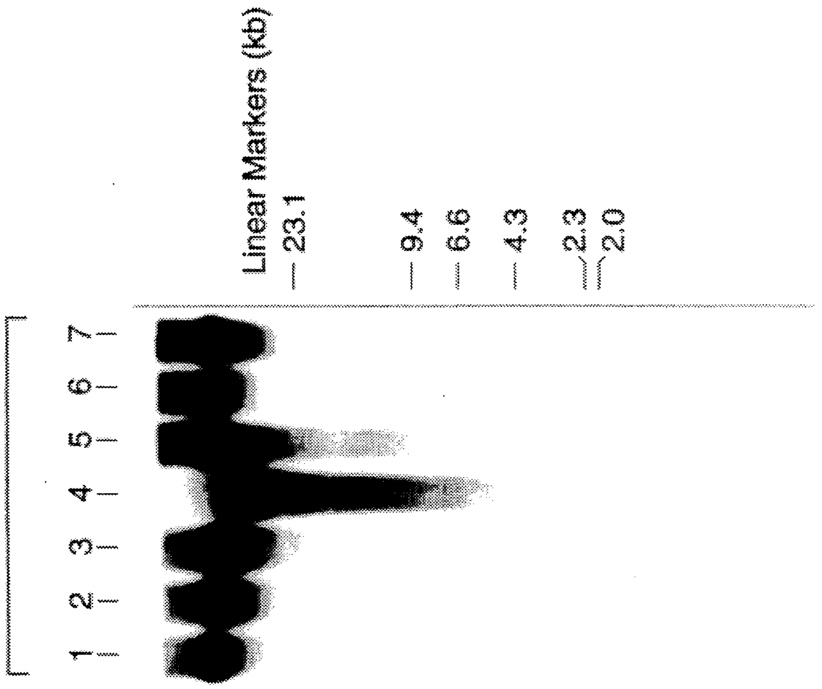
FIG. 3B is an autoradiograph of the same gel after blotting to nitrocellulose and hybridization with the $^{32}$P-labeled 6.3 Kb EcoRI fragment from pSPR33 (panel B). Lanes 1 are TX1352; lanes 2 are CT26816; lanes 3 are CT27985; lanes 4 are CA-3087; lanes 5 are CT21343; lanes 6 are CT20004; and lanes 7 are Sh-2-82. Note the strong hybridization signal associated with the chromosomal band.
Figure 3A:
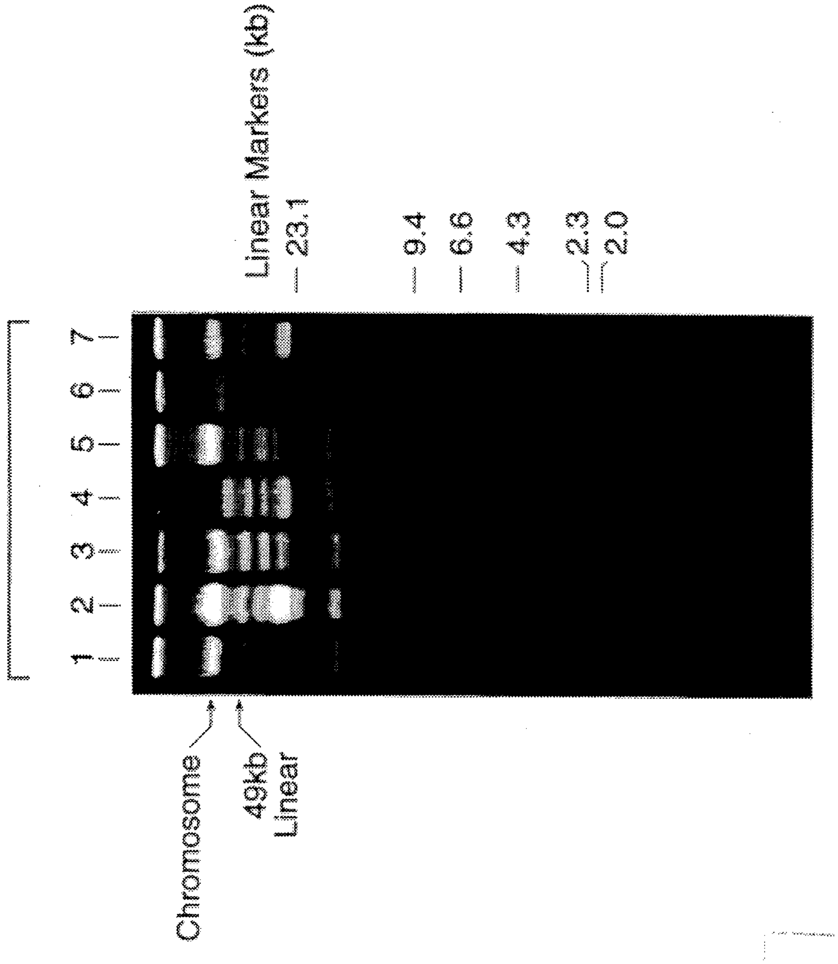
FIG. 3A is an ethidium bromide stained gel of undigested total DNA from 7 isolates of *B. burgdorferi* (panel A)

Southern blot analysis of undigested DNA from seven similar isolates, indicated that the 6.3 Kb fragment hybridized strongly with chromosomal DNA (FIG. 3A and 3B). Undigested total DNA was electrophoresed in 0.4% agarose gels (12 v for 16 hrs). Southern blot procedures including the transfer of DNA from agarose gels to nitrocellose, high stringency hybridization (which permitted 10% basepair mismatch), and autoradiography were as previously described (Spanier et al. 1983. Virology 130:514–522) except that the prehybridization and hybridization buffers and temperatures were as described by Schwan et al. (Schwan et al. 1989. J. Clin. Microbiol. 27:1734–1738).

The DNA probe was recovered from agarose gels using Gene Clean (BIO 101, Inc., La Jolla, Calif.) and labeled with [α-$^{32}$P]dCTP (3,000 Ci/mmol) by nick translation according to the directions of the manufacturer (Nick Translation Kit, Bethesda Research Laboratories, Gaithersburg, Md.). The probe was boiled for 4 min. and quenched on ice immediately before adding to the hybridization buffer.

Restriction endonucleases were purchased from Boehringer Mannheim Biochemicals, Indianapolis, Ind., and digestions were performed as recommended by the manufacturer.

The smeared band in agarose-gels that contained heterogenous fragmented DNA and migrated slightly slower than the 49 Kb linear plasmid from strain Sh-2-82 was assumed to be chromosomal DNA. Total DNA from 5 additional Borrelia species including *B. hermsii, B. parkeri, B. anserina, B. turicatae,* and *B. coriaceae* did not hybridize to the 6.3 Kb fragment (FIG. 2). These data indicate that the pSPR33 insert sequences are chromosomally located and are specific to *B. burgdorferi.*

Example 2. Immunoblot Analysis of Cloned B. burgdorferi Proteins

To identify the specific proteins encoded by pSPR33 that reacted with the human serum used to screen the library, whole-cell lysates of E. coli carrying pSPR33 were analyzed by SDS-PAGE and immunoblot.

Rabbit serum prepared against whole-cell lysates of E. coli carrying either pSPR33 (anti-pSPR33) or the vector pBluescript SK (anti-E. coli) were prepared as follows. Bacterial cells recovered from 16 hr cultures, were washed once and resuspended in phosphate buffered saline (PBS) to a final concentration of $10^8$ cells/mi. The cells were killed by incubating for 30 min. at 56° C. and disrupted by sonication on ice (2 min. at an output of 4; Branson Sonifier-Cell Disrupter 185). New Zealand white rabbits were immunized (without adjuvant) intramuscularly with 1.5 ml of the cell sonicate and boosted with the same immunogen at 21 and 42 days after the primary immunization. Sera were collected every 2 weeks thereafter for 4 months, pooled, and 5 ml aliquots absorbed with E. coli strain XL1-blue cells (Stratagene) collected from 500 ml cultures and incubated with rotation at 37° C. for 4 hr. The bacteria were removed by centrifugation in a VTi80 rotor at 40,000 rpm for 30 min. This process was repeated twice, and absorbed sera were then filtered through a sterile 0.22 μm filter (Millipore Corp., Medford, Mass.) and stored at −20° C. Anti-pSPR33 and anti-E. coli sera was used at a dilution of 1:500 and 1:50 respectively. The monoclonal antibodies H5332 (Barbour et al. 1983. Infect. Immun. 41:795–804), H5TS (Barbour et al. 1984. Infect. Immun. 45:94–100), and H9724 (Barbour et al. 1986. Infect. Immun. 52:549–554) were used at a dilution of 1:100.

IFA titers of Lyme borreliosis and relapsing fever sera were determined as previously described (Burgdorfer et al. 1982. Science 216:1317–1319). *B. burgdorferi* strain B31 and *B. hermsii* strain HS1 respectively were used as the antigens in the IFA tests.

Immunoblot analysis of whole-cell lysates were performed essentially as previously described (Schwan et al. 1989. Infect. Immun. 57:3445–3451) except cells were prepared as follows. Cells were recovered from liquid cultures by centrifugation (8,000 xg for 5 min), and resuspended in PBS to give an optical density of 0.2 at 600 nm. Cells from 2 ml of this suspension were recovered by centrifugation and resuspended in 100 μl of distilled water and 50 μl of sample buffer (0.2M Tris, pH 6.8; 30% (v/v) glycerol; 3% (w/v) SDS; 0.002% (w/v) bromophenol blue). Samples were then boiled for 4 min. and 20 μl loaded onto a 12.5% SDS-PAGE gel. Gel electrophoresis, immunoblotting and detection of bound antibody, using $^{125}$I protein A, have been described (Schwan et al. 1989. Infect. Immun. 57:3445–3451).

Figure 4:
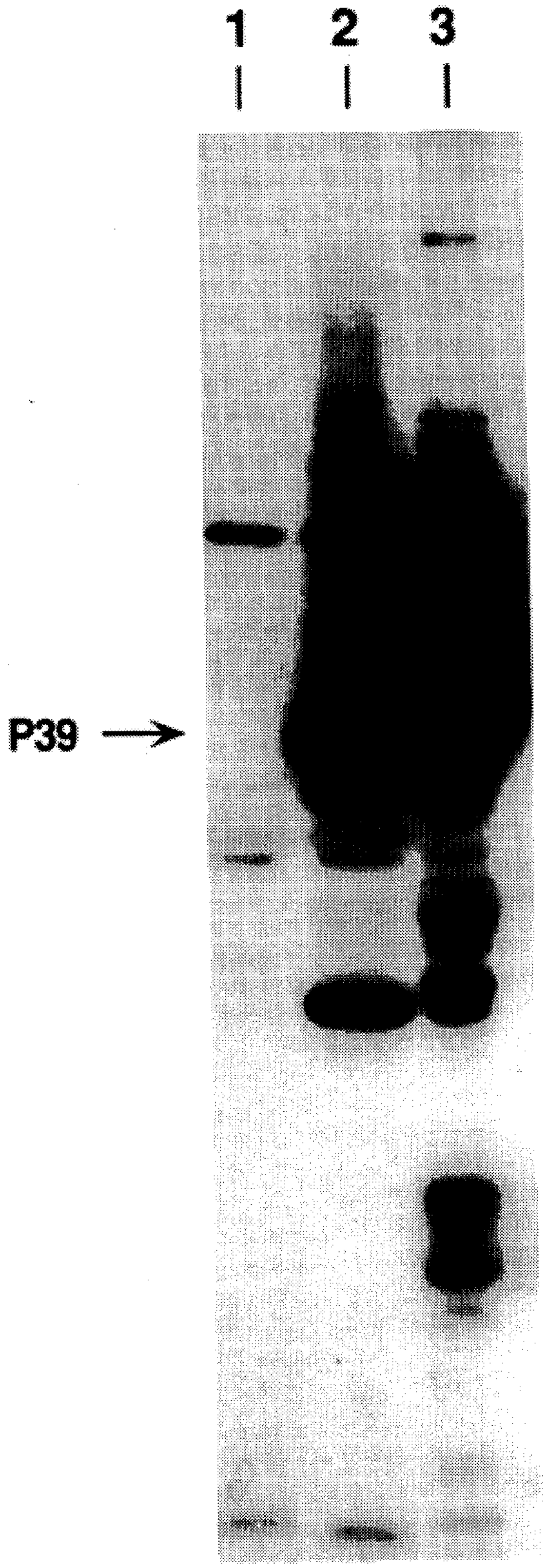
FIG. 4 shows immunoblot analysis of proteins expressed by pSPR33. Whole-cell lysates of *B. burgdorferi* strain Sh-2-82 (lane 3), E. coli carrying pSPR33 (E. coli+pSPR33) (lane 2) and E. coli carrying only vector (E. coli+vector) (lane 1) were immunoblotted with the human Lyme borreliosis serum used to screen the DNA library of *B. burgdorferi.*

A 28 kDa (P28) and a 39 kDa (P39) antigen in the pSPR33 immunoblot profile, were the most immunoreactive antigens that were not detected in lysates of E. coli cells carrying only the vector (FIG. 4). Antisera raised to whole-cell lysates of E. coli carrying only the vector (anti-E. coli serum) did not react with P28 or P39 at a dilution of 1:50. These two proteins, therefore, are antigenically unrelated to native E. coli components and appear to be encoded by the cloned Borrelia sequences. P28 and P39 could not be resolved in SDS-PAGE gels stained with either Coomassie blue or silver nitrate because they co-migrate with other, more abundant E. coli proteins.

Figure 5:
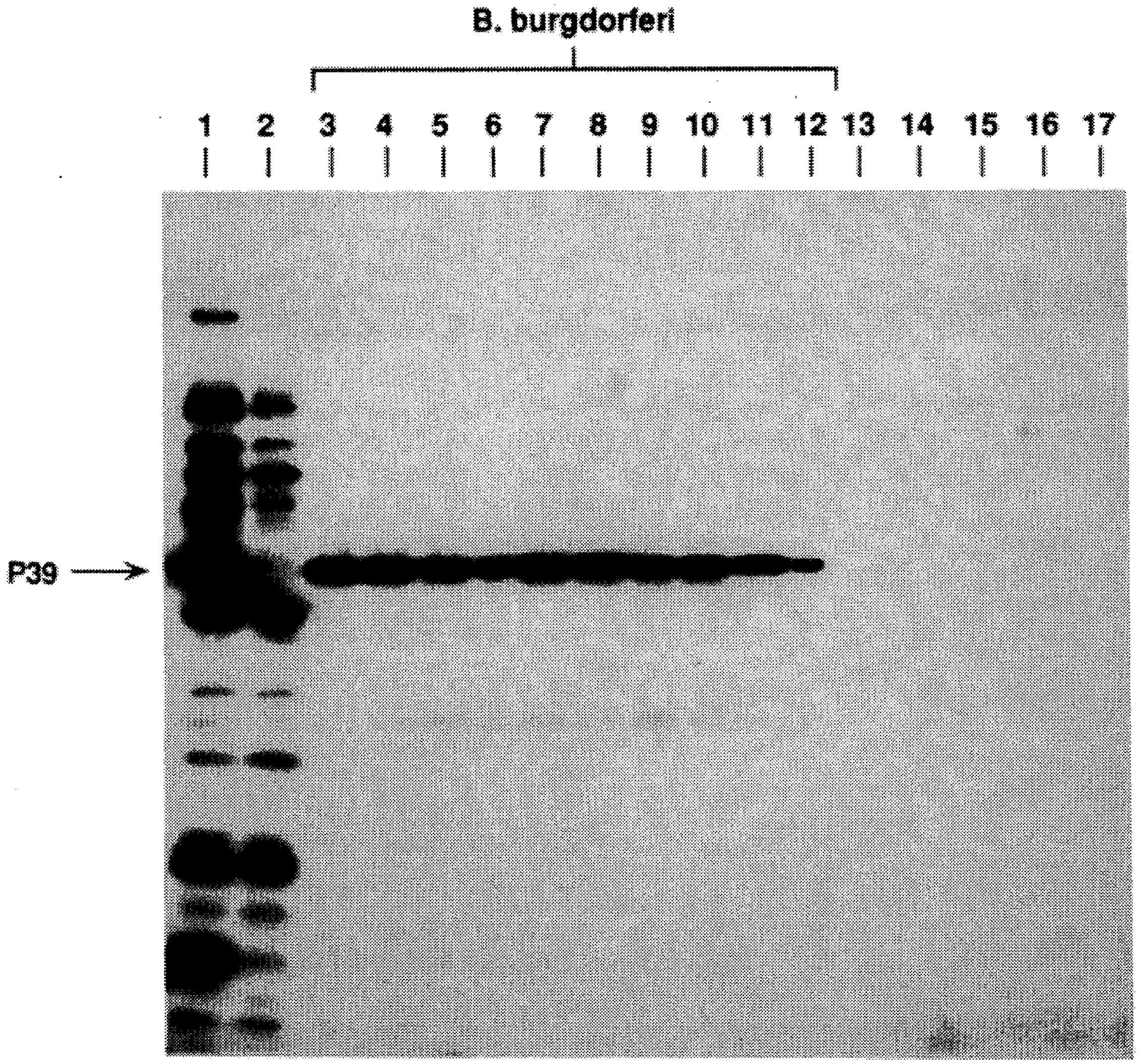
FIG. 5 demonstrates the specificity of P28 and P39 expression in *B. burgdorferi.* Whole-cell lysates of different

Similar sized proteins to P28 and P39 were detected by immunoblot (FIG. 4) in cell lysates of *B. burgdorferi* strain Sh-2-82, suggesting P28 and P39 are expressed by this strain. To determine if the 28 and 39 kDa Borrelia proteins seen in whole cell lysates were identical to the gene products P28 and P39 respectively, antiserum generated to cells carrying pSPR33 (anti-pSPR33 serum) was incubated with Western blotted whole-cell lysates of 1 European and 19 North American *B. burgdorferi* isolates, and compared to a lysate of E. coli producing P28 and P39 (FIG. 5). All of the 20 Borrelia isolates expressed a 39 kDa protein that comigrated with P39. A 28 kDa protein was also detected, but considerably less antibody bound this protein than that which bound P39. P39 produced by pSPR33 also reacted with sera from five white-footed mice (*Peromyscus leucopus*) experimentally infected with *B. burgdorferi* strain Sh-2-82, but did not react with the preimmune sera from these animals, or with sera from mice infected only with E. coli. Other species of Borrelia did not produce detectable amounts of P28, P39 or any other antigenically related proteins under the conditions employed (FIG. 5). Extended exposure (>24 hours) of autoradiographs revealed weak bands with molecular weights other than 28 kDa and 39 kDa in all Borrelia profiles, but these are attributed to nonspecific binding. Data, including the fact that DNA from other species of Borrelia lacked sequences with close identity to those that encode P28 and P39 (FIG. 2), show that P28 and P39 are proteins specific to *B. burgdorferi*. Furthermore, anti-pSPR33 did not react with the *B. burgdorferi* antigens Osp A (31 kDa), Osp B (34 kDa) or the 41 kDa flagellin, suggesting that these proteins are antigenically unrelated to P28 and P39 (FIG. 5).

To confirm this, it was shown that the monoclonal antibodies H5332, H5TS and H9724 (FIG. 6), which bind specifically to Osp. A (Barbour et al. 1983. Infect. Immun. 41:795–804), Osp B (Barbour et al. 1984. Infect. Immun. 45:94–100) and the flagellin (Barbour et al. 1986. Infect. Immun. 52:549–554) respectively, did not bind to P28 or P39 produced by either pSPR33 or strain Sh-2-82. The specificity of monoclonal antibody H9724 for *Borrelia flagellin* is evident in FIG. 6, as this monoclonal only bound a 41 kDa band in the *B. burgdorferi* profile and a 39 kDa band, which corresponds to its flagellin (Barbour et al. 1986. Infect. Immun. 52:549–554), in the *B. hermsii* profile. Furthermore, using electron microscopy and colloidal gold staining, monoclonal antibody H9724 bound to endoflagellin from *B. burgdorferi* whereas anti-pSPR33 did not.

Example 3. Immunoreactivity of Lyme Borreliosis Sera with Cloned Borrelia Proteins To test the possibility that P28 and P39 are immunodominant proteins, ninety-four human sera collected from patients clinically diagnosed as having Lyme borreliosis were tested for reactivity with cloned P28 and P39 at a dilution of 1:100. Whole-cell lysates were electrophoresed in SDS-PAGE gels and Western blotted as previously described in the above Examples. The nitrocellulose was cut into equal strips (5 per gel) such that each strip contained lanes for E. coli carrying pSPR33, E. coli carrying only the vector and *B. burgdorferi* strain Sh-2-82. Each strip was incubated with a different human serum except for one strip from each gel which was incubated with anti-pSPR33 serum. This latter strip served as marker for the positions of P28 and P39. All of 33 sera with IFA titers ≧1:256 (100%), 13 of 17 sera (76%) with IFA titers=1:128, and 14 of 44 sera (32%) with titers ≦1:64 reacted with P39 (see Table 2 below).

TABLE 2

Summary of human Lyme borreliosis sera tested for reactivity with P39

| IFA Titer Percent Sera Positive | No. Sera Tested | No. Sera Reacting with P39 |
|---|---|---|
| ≧1:2048 100 | 5 | 5 |
| 1:1024 100 | 8 | 8 |
| 1:512 100 | 9 | 9 |
| 1:256 100 | 11 | 11 |
| 1:128 76 | 17 | 13 |
| 1:64 40 | 10 | 4 |
| 1:32 55 | 9 | 5 |

TABLE 2-continued

Summary of human Lyme borreliosis sera tested for reactivity with P39

| IFA Titer Percent Sera Positive | No. Sera Tested | No. Sera Reacting with P39 |
|---|---|---|
| ≦1:16 | 25 | 5 |
| 20 | | |
| Total | 94 | 60 |

Examples of immunoblots for human sera reacting with P39 (arrow 1) are shown in FIGS. 7A and 7B. A strongly reacting 58–65 kDa band was observed in the *B. burgdorferi* profile (FIG. 7A band A) for all sera that reacted with P39, but since anti-pSPR33 serum does not react to a band in this region of the gel (FIG. 5), P39 and the 58–65 kDa protein(s) are presumably unrelated. Although P28 appeared to react strongly to some sera (FIG. 7B, band B), for other, less reactive sera, it was not clear if the sera reacted to P28 or to some other protein. This was because these sera also reacted with co-migrating E. coli proteins that were detected with a longer autoradiographic exposure (FIG. 7A, band B). Therefore, although it is not clear to what extent P28 actually reacts with human Lyme borreliosis sera, it appears that antibody to P39 was detected in 100% of all sera that had IFA titers≧1:256. Notably, many sera reactive to P39 did not appear to react with the 41 kDa flagellin (FIG. 7A & 7B). In view of this, antibody to P39 could be mistaken as antibody to the flagellin when testing human sera by immunoblot using whole-cell lysates of *B. burgdorferi*. Because P39 was shown to be specific to *B. burgdorferi* by immunoblot, it is not surprising that control sera, which included sera from 5 ALS patients, 5 syphilitic patients, 5 relapsing fever patients and 10 normal individuals who showed no symptoms of clinical disease, did not react to the cloned P39 protein at a dilution of 1:50 (see Table 3 below). Immunoblot findings for the syphilitic sera are shown in FIG. 8. These data suggest that P39 has antigenic specificity for sera collected from patients with Lyme borreliosis. This is despite the fact that both the syphilitic and relapsing fever sera tested had significantly high IFA Lyme borreliosis titers (see Table 3 below), and therefore most likely contained cross-reacting antibodies directed at other *B. burgdorferi* antigens.

TABLE 3

Summary of IFA titers for control sera that did not react with P39.

| Serum description plasma test | Lyme IFA | Relapsing fever IFA | Rapid reagin (1) |
|---|---|---|---|
| Syphilitic | | | |
| 1 | 1:128 | 1:256 | 1:128 |
| 2 | 1:256 | 1:1024 | 1:128 |
| 3 | 1:1024 | 1:2048 | 1:128 |
| 4 | 1:512 | 1:1024 | 1:64 |
| 5 | 1:128 | 1:1024 | 1:32 |
| Relapsing fever | | | |
| 1 | 1:1024 | 1:1024 | — |
| 2 | 1:32 | 1:512 | — |
| 3 | 1:128 | 1:512 | — |
| 4 | 1:64 | 1:512 | — |
| 5 | 1:64 | 1:1024 | — |
| ALS | | | |

TABLE 3-continued

Summary of IFA titers for control sera that did not react with P39.

| Serum description plasma test | Lyme IFA | Relapsing fever IFA | Rapid reagin (1) |
|---|---|---|---|
| 1 | 1:16 | 1:64 | — |
| 2, 3, 4 | <1:16 | <1:16 | — |
| 5 | 1:16 | 1:16 | — |
| Normal | | | |
| 1, 2, 3, 4 | <1:16 | 1:16 | — |
| 5, 6, 7, 8 | <1:16 | <1:16 | — |
| 9, 10 | <1:16 | 1:32 | — |

1 = Portnoy, 1963. Amer. J. Clin. Pathol. 40:473–479

The immunodominance of P39 and this antigens' potential to be a virulence factor of *B. burgdorferi* on account of its immune characteristics and association with infectivity, lead to further characterization of the genetic basis for P39 expression.

Example 4. PSPR 33 Subclone and deletion analysis. Eleven subclones were constructed to determine the approximate position of the P39 locus in the 6.3 kb EcoRI insert in the parent construct pSPR33. The endonucleases EcoRI, ClaI, HindIII, BamHI and PstI were used according to the manufacturer (Boehringer Mannheim Biochemicals) to produce various restriction fragments, which were then ligated to the linearized pBluescript cloning vector (Stratagene) cut with the appropriate enzyme or combination of enzymes. A 4.4 kb EcoRI—ClaI fragment was ligated into the vector and transformed into DH5 alpha Escherichia coli competent cells (Bethesda Research Laboratories) and designated pSPR38 (FIG. 9). A 2.3 kb EcoRI—HindIII fragment produced the subclone pSPR45; a 5.0 kb BamHI fragment produced the subclone pSPR46; a 3.3 kb PstI fragment produced the subclone pSPR44; a 1.4 kb PstI fragment produced the subclone pSPR42. Additional subclones were produced as deletion products by deleting sequences from the HindIII end of the EcoRI—HindIII DNA fragment in the subclone pSPR45. Once digested with HindIII, Dnase was applied for increasing lengths of time to shorten the fragment. The new end was treated with DNA polymerase and nucleotides were added to blunt the end for ligation into linearized, blunt-ended vectors (pBluescript). By successive treatments, the subclones pSPR51, pSPR54, pSPR57, and pSPR59 were constructed (FIG. 9).

To determine whether the clones were expressing P39, expression assays of the P39 deletion and subclone variants (FIG. 9) were performed with polyclonal anti-P39 serum (anti-pSPR33, previously described), monoclonals A6 and D1 and Western blotted whole-cell lysates. Two monoclonal antibodies to P39 antigen were produced using standard techniques for one of ordinary skill in the art. Escherichia coli cells containing the recombinant pSPR33 were inoculated intraperitoneally into BALB/c laboratory mice. After one month, the mice were boosted with an identical inoculum. One week after the boost, serum samples from the mice were tested by Western blot analysis for anti-P39 antibodies and mice seropositive were again boosted with recombinant E. coli. After three days, spleen were removed. Spleen cells were separated and fused with hybridoma cells SP-20 in HY culture media, 37° C., 8% $CO_2$. Successful fusions were then cloned by limiting dilution in 96-well microtiter plates. Tissue culture supernatants of positive cell cultures were then tested by Western blot analysis for anti-P39 antibody. Two clones positive for such analysis, designated A6 and D1, were used in subsequent analysis of P39 antigen and the expression of various subclones of pSPR33 as previously described.

To examine various antisera and monoclonal antibodies by Western blot analysis for anti-P39 antibodies, the E. coli recombinant with pSPR33 was first lysed by heat in 2-mercaptoethanol and then electrophoresed in a 12.5% SDS-polyacrylamide gel for 6 hr. The gel was then electroblotted with the Towbin system for 3 hr. to transfer the E. coli recombinant proteins onto a nitrocellulose membrane. After transfer, the membrane was blocked with TSE-Tween to reduce the nonspecific binding of immunoglobulins. Next the membrane was immersed in the appropriate test serum or monoclonal antibody and incubated at room temperature with rocking for 1 hr. The membrane was then rinsed with water and incubated next in a solution of $^{125}$I-protein A to label antibodies bound to the antigens on the membrane. After incubation and washing off the excess label, the membrane was dried and placed on Kodak XAR-5 film for autoradiographic detection of the anti-P39 antibodies. Similar assays were conducted for the other subclones.

Plasmids pSPR38 and pSPR46 expressed the same amount of P39 as the primary clone pSPR33. This, along with the fact that plasmid pSPR51 expressed P39 whereas pSPR54 did not, we conclude that the gene for P39 was between the RamHi and HindIII sites (FIG. 9, black bar). The amount of P39 associated with cell lysates of clones pSPR51 and pSPR45 is less than the other clones that were P39 positive. This suggested that sequences to the right of the gene locus were important for full expression. P39 was produced by a clone (pSPR46) that contained the insert in the opposite orientation to that of other P39 producing clones (e.g. pSPR38). Therefore, expression of P39 was not dependent on the Lac promoter (FIG. 9, back arrows). The pstl fragment that was subcloned from pSPR33 and designated pSPR44 (FIG. 9), did not express detectable amounts of P39. Thus, the P39 gene was assumed to be transcribed from left to right. We presume that the additional sequences correspond to the second of two genes that express similar but distinct antigens and that they collectively augment the amount of antibody that binds the 39 kDa band in the immunoblot assay. Because the plasmid pSPR44 did not express any antigens reactive with polyclonal anti-P39 serum, the expression of the second gene located to the right of the black box (FIG. 9) may depend on the transcription of the first gene.

Example 5. DNA sequencing of the gene encoding P39. The DNA sequence (FIG. 10A) was determined for the BamHI-HindIII fragment (FIG. 9, black box) by the strategy summarized in FIG. 11*b*. Essentially, sequence was obtained using primers designed from DNA sequence determined using the universal M13 primer and the subclones pSPR46, pSPR44, and pSPR45, and the Mung Bead nuclease deletion variants pSPR51, pSPR54, pSPR56, and pSPR57, of plasmid pSPR45. DNA sequence to the right of the HindIII restriction site was determined using primers designed from existing sequence information.

DNA sequence was obtained first by using primers designed for use with the M13 universal primer and available sequence of the cloning vector. The protocol for performing the sequencing reactions was exactly that provided by United States Biochemical (Sequenase—Version 2.0: Step-By-Step Protocols for DNA Sequencing With Sequenase® Version 2.0—5th Edition). Sequencing reactions were run in small plastic centrifuge tubes. Each reaction volume was 10Nl and included primer, buffer and DNA to anneal primer to template. Labeling was done by adding Sequenase, 35S-dATP, and additional buffer. Termination of the A, T, G, and C reactions was done by adding a stop solution. Samples were then heated to 70°–80° C. for two minutes and then 2–3 Nl of each mix was added to each lane of the gel. All sequencing gels were 6% acrylamide—7M urea—1×TBE and were run for 2 hr or 4 hr. After running, the gels were fixed in 5% acetic acid —15% methanol to remove urea. Gels were then dried at 80° C. under vacuum then placed on Kodak XAR-5 film. Exposed films were then analyzed for autoradiographic bands to determine the sequence. Terminal sequences of each reaction were used to generate new oligo-nucleotide primers for use in the next sequencing reactions. Therefore, the entire sequences of each strand of DNA were determined through successive extensions using primers determined by previous reactions. By way of example, synthetic primers of 20 nucleotides from a region of SEQ ID no. 1 can be constructed and utilized to sequence about 300 bases. Other primers can then be constructed from the deduced sequence. Such techniques are standard and would be known to one of ordinary skill in the art.

Analysis of the completed DNA sequence (SEQ. ID No. 1) revealed two open reading frames (FIG. 10A). Gene 1 was in frame 1 and gene 2 was in frame 3. No other significant open reading frames were detected. The DNA sequence has been numbered from the adenine residue of the ATG start codon for the protein encoded by gene 1 because it is assumed that this is the first gene transcribed. This open reading frame (nucleotides 1 to 1020) was confirmed by sequencing the first 15 amino acids of P39 expressed by clone pSPR51. This clone has had gene 2 deleted, and therefore its gene product was not detected during protein sequencing. Gene 1 corresponds to a protein of 339 amino acids with a calculated molecular weight of 36,926 kDa. Because this gene encodes a protein that reacted with all of 10 serum specimens collected from: human Lyme patient but not to 10 normal controls specimens (data not shown), it assumed that this protein is equivalent to P39. Because of the existence of a second gene product with a similar molecular weight that may also bind human serum, it was determined that the P39 antigen as previously described is not one protein but two proteins (39α and 39β). This is suggested by the expression data shown in FIG. 9, where the P39 signal appears to be enhanced if both genes are present. The open reading frame (nucleotides 1107 to 2132) of gene 2 has been designated p39β. This genes open reading frame begins 116 nucleotides down stream of p39β and encodes a protein of 341 amino acids (37.506 kDa). A promoter 5' to the start codon in p39α appeared to be present with classic −10 and −35 regions whereas the p39β lacked recognizable promoter sequences. Both genes, however, had putative ribosomal binding sites immediately 5' to the start codons and each was terminated with a TAA codon at positions 1018 and 2130 respectively. The putative promoter and ribosomal binding sites resemble those associated with other genes from *B. burgdorferi* including the opsA-operon and the flagellin gene (Wallich, R., S. E. Moter, M. M. Simon, K. Ebnet, A. Heiberger, and M. D. Kramer, 1990. The *Borrelia burgdorferi* flagellum-associated 41 kilodalton antigen (flagellin); molecular cloning, expression and amplification of the gene. Infect Immun 58:1711–1719). Unlike the genes encoding the flagellin, OspA and OspB, no stem loop structures were detected at the 3' end of either p39α and p39β, suggesting termination may be outside what has been sequenced. Nevertheless, in accordance with the transcription termination regions in many bacteria, including Borrelia, this region is AT rich, suggesting that termination is in the vicinity of nucleotide 2170.

Comparing the DNA sequence of p39α and p38β by the Needleman and Munsch global alignment program (Needleman and Munsch, J. Mol. Biol.; 148:443–53 (1970)), indicates that these genes have 62% DNA sequence similarity. No significant sequence similarity was detected between the P39 genes and either the OspA-OspB operon or the flagellin gene. Codon preference and G+C content analysis of the p39 operon indicated that there were no significant differences between it and the other Borrelia genes.

Example 6. Determination of p39α and p39β transcript size.

Northern blot analysis (FIG. 12) of total RNA from *B. burgdorferi* strains B31 and Sh-2-82 were probed with a PstI-HindIII fragment internal to the p39α and p39β loci (FIG. 11). This probe detected a single 2.35 kb message, and tends-to confirm that the P39α and β mRNA is polycistronic and that p39α and p39β constitute an operon (p39). This conclusion is supported by the DNA sequence data described above which shows that p39β does not appear to have a recognizable promoter. Furthermore, this explains why clones that carry an intact p39β but lack the promoter for p39α (eg. pSPR44), do not express antigens reactive with polyclonal anti-P39 serum (anti-pSPR33) (FIG. 9). As a control for specificity, total RNA from E. coli was shown not to hybridize to the PstI-HindIII Borrelia fragment (FIG. 12). The amino acid composition of P39α and P39β are similar (SEQ. ID. No. 2 and 3, Table 4), although distinct from the amino acid composition of OspA and OspB. P39 and P39β contained comparatively much larger amounts of isoleucine, proline, arginine, phenylalanine, tyrosine, and methionine. Furthermore, lysine and threonine, which are present in large amounts in OspA and OspB, constitute a much smaller proportion of P39α and P39β. Between P39α and P39β, the major difference was the 3 cysteine residues in the later protein and 4 histidine residues in the former protein (Table 4).

TABLE 4

Amino acid composition of proteins encoded by the P39 operon

| | P39α(%) | P39β(%) |
|---|---|---|
| Alanine | 25 (7.4) | 22 (6.5) |
| Cysteine | 1 (0.3) | 3 (0.9) |
| Aspartic acid | 20 (5.9) | 21 (6.2) |
| Glutamic acid | 26 (7.7) | 21 (6.2) |
| Phenylalanine | 16 (4.7) | 16 (4.7) |
| Glycine | 33 (9.7) | 32 (9.4) |
| Histidine | 4 (1.2) | 1 (0.3) |
| Isoleucine | 37 (10.9) | 43 (7.6) |
| Lysine | 30 (8.8) | 26 (7.6) |
| Leucine | 32 (9.4) | 26 (7.6) |
| Methionine | 5 (1.5) | 6 (1.8) |
| Asparagine | 17 (5.0) | 21 (6.2) |
| Proline | 8 (2.4) | 7 (2.1) |
| Glutamine | 4 (1.2) | 7 (2.1) |
| Arginine | 7 (2.1) | 9 (2.6) |
| Serine | 29 (8.6) | 30 (8.8) |
| Threonine | 12 (3.5) | 5 (1.5) |
| Valine | 18 (5.3) | 25 (7.3) |
| Tryptophan | 1 (0.3) | 2 (0.6) |
| Tyrosine | 14 (4.1) | 18 (5.3) |
| | 339 | 341 |

P39β, line OspA and OspB, has a classic signal peptide including the putative cleavage site defined by the tetrapeptide Leu-X-X-Cys (FIG. 13), where X usually represents any neutral amino acid. For P39β, the leu residue is at position 12 and the cysteine at position 15 (SEQ. ID. No. 1). Although P39α also has a hydrophobic N-terminus (FIG. 14A) and a cysteine at a similar position (position 18), this protein does not have the tetrapeptide, suggesting that its putative signal sequence is processed in a different manner to that of the corresponding region in P39β. Because P39α and P39β have a cysteine at close to the same position as the cysteine in OspA and OspB, and it has been predicted that the latter two proteins are acylated at the site, P39α and P39β may also be lipoproteins due to acylation of their N-terminal cysteine residue.

Comparing the amino acid sequence of P39α and P39β revealed 52% sequence identity. This is similar to the reported 53% similarity between OspA and OspB. Surprisingly and in contrast to that found for OspA and OspB, the p39 operon proteins have very similar hydropathy plots (FIG. 14A). This, along with the high degree of sequence similarity, indicates that the two proteins share a considerable number of the same epitopes having immunogenic properties. Antiserum raised to OspA will react to OspB, indicating proteins like P39α and P39β with significant identity at the amino acid level will share cross-reactive epitopes.

The genetic element encoding the immunodominate antigen P39 was identified and sequenced. This element was shown to be two genes that constituting an operon encoding two similar sized proteins, P39α and P39β, that have considerably amino acid sequence similarity. This is the first report of an operon encoding putative membrane proteins that has a chromosomal origin in *B. burgdorferi*. It is assumed that both the –α and β forms contribute to the signal when antibody from infected animals binds the P39 band in Western blots (Simpson, W. J., W. Burgdorfer, M. E. Schrumpf, R. H. Karstens, and T. G. Schwan, 1991. Antibody to a 39 kDa *Borrelia burgdorferi* antigen (P39) as a marker for infection in experimentally and naturally inoculated animals. J Clin Microbio 29:236–243. Simpson, W. J., M. E. Schrumpf, and T. G. Schwan, 1990. Reactivity of human Lyme borreliosis sera with a 39-kilodalton antigen specific to *Borrelia burgdorferi. J Clin Microbiol* 28:1329–1337). This raises the question of whether all Lyme serum reacts equally well to both α and β forms or whether some serum reacts to one and not the other.

The function of P39α and P39β is not known, but several characteristics, deduced from the predicted amino acid sequence suggests several possibilities. These proteins exhibit alternating hydrophobic and hydrophilic regions, characteristic of an amphophilic or transmembrane protein. In accordance with a membrane location, immune electron microscopy analyses of *B. burgdorferi* with monoclonal antibody A6 indicates that the P39 antigen is in or associated with the membranes (unpublished data).

P39β resembles OspA and OspB in that it has typical signal sequence and cleavage site at the first cysteine residue. Like OspA and OspB, P39β is probably membrane associated and may be acrylated at the N-terminal cysteine. P39α, however, is different with regard to its signal sequence which may not be cleaved because it lacks the type 1 recognition site. If so, P39α may be secreted and therefore the antigen that stimulates the immune response during an infection. This notion would help to explain the earlier observation that anti-P39 antibodies appear to more readily associated with the infected state, because a secreted form could accumulate more rapidly during the early stages of an infection than that associated with cells. (Simpson, W. J., W. Burgdorfer, M. E. Schrumpf, R. H. Karstens, and T. G.

Schwan, 1991. Antibody to a 39 kDa *Borrelia burgdorferi* antigen (P39) as a marker for infection in experimentally and naturally inoculated animals. J Clin Microbiol 29:236–243.)

Example 6: Amplification of gene 1 (P39α) and gene 2 (P39β)

To determine the immunoreactiveness both P39α and P39β, gene 1 and gene 2 will be cloned separately and the expression products examined for their reactivity with Lyme immune sera. Standard methodologies for cloning and expressing each gene can be employed; however, it is preferred to amplify each gene separately using the polymerase chain reactive (PCR) and the primer sequences identified in SEQ. ID Nos. 4–7.

The synthetic oligonucleotide DNA primers described were constructed with an Applied Biosystems Inc. DNA Synthesizer Model 380-B, following the instructions provided by the manufacturer. In this procedure, short chains of nucleotides of a specific order are produced in a concentrated ammonium hydroxide solution. This material is then centrifuged under vacuum to remove the ammonium hydroxide. The dry DNA pellet is then resuspended in TE buffer and the DNA concentration is determined by spectrophotometric absorbance at 260 mm. Concentrations of the DNA primers are then standardized for PCR according to the protocol provided by Perkin-Elmer-Cetus.

To amplify *B. burgdorferi* DNA by PCR using the primers described, the protocol involves mixing the *B. burgdorferi* DNA with either primers 1 and 2 for gene 1 (sequences 4 and 5), primers 1 and 2 for gene 2 (sequences 6 and 7), and sequences 4 and 7 to amplify both genes 1 and 2 together. Also added to the PCR mix is the DNA Taq polymerase, buffer, and the mixture of the four nucleotides (dNTPs). This reaction mixture is then subjected to repetitive cycles of three different temperatures to cause denaturing the DNA, annealing of the primers to the template DNA, and extension (polymerization) to produce a new strand of DNA. After 30 cycles using the thermal cycler, the PCR amplification products are examined by running 10 μl of each sample in an electrophoresis agarose gel.

In order that the amplified products can be inserted into known vectors by standard techniques known to a skilled artisan, at the 5' end of each primer, nucleotides will be added that encode for the recognition site for the restriction endonuclease EcoRI (G/AATTC).

The amplified DNA products will be comprised of each gene with the addition of an EcoRI site at each end, which will allow us to insert this sequence into any one of many available cloning and expression vectors which have only one EcoRI site available, such as pUC, pBluescript, pBR322, etc. The vectors are inserted into host cells to obtain expression of the DNA products. Such techniques are well known to one of ordinary skill in the art.

Next, recombinants having the appropriate sized inserted DNA (1017 bases for gene 1; 1023 bp for gene 2) will be examined by Southern blot analysis to identify the cloned fragments. DNA from recombinants with the presumptive gene 1 or gene 2 will be separated in agarose gels, transferred to nitrocellulose membranes, and probed with the purified EcoRI fragment from pSPR33. Such procedures are standard techniques well known to anyone skilled in the art. After confirming that the amplified cloned fragments are homologous with the pSPR33 insert, the various clones are tested for expression of P39 antigens using standard Western immunoblotting techniques. Rabbit anti-pSPR33 antiserum, anti-P39 monoclonal antibodies (as previously described), and convalescent serum from human Lyme patients will each be reacted with whole-cell lysates of the various clones to identify and obtain expression products of each gene. The synthetic peptides can be mapped to identify specific immunoreactive epitopes, used in bioassays to detect Lyme borreliosis disease or used in vaccines for mammals against Lyme borreliosis disease.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A bioassay for the diagnosis of Lyme borreliosis disease comprising the steps of:

i) coating a surface with purified antibodies raised against at least one recombinant non-flagellar *Borrelia burgdorferi* protein having a molecular weight of about 39 kD, wherein said protein is specifically immunoreactive with *Borrelia burgdorferi,* and is expressed from a *Borrelia burgdorferi* DNA fragment having SEQ. ID No 1, and forming a coated surface;

ii) contacting said coated surface with serum from a mammal suspected of having Lyme disease; and iii) detecting the presence or absence of a complex formed between said antibodies and proteins present in said serum, the presence of the complex indicating a positive diagnosis of Lyme borreliosis.

2. The bioassay according to claim 1, wherein said surface is coated with purified antibodies raised using at least one recombinant non-flagellar *Borrelia burgdorferi* protein having a molecular weight of about 39 kD, wherein said protein is specifically immunoreactive with *Borrelia burgdorferi,* and is expressed from a *Borrelia burgdorferi* DNA fragment of pSPR33 having ATCC No. 68243.

3. A bioassay for diagnosis of Lyme borreliosis comprising the steps of:

i) coating a surface with purified antibodies raised against at least one recombinant non-flagellar *Borrelia burgdorferi* protein having a molecular weight of about 39 kD, wherein said protein is specifically immunoreactive with *Borrelia burgdorferi*, and is expressed from a *Borrelia burgdorferi* DNA fragment having SEQ ID Nos. 2 or 3 and forming a coated surface;

ii) contacting said coated surface with serum from a mammal suspected of having Lyme disease; and iii) detecting the presence or absence of a complex formed between said antibodies and proteins present in said serum, the presence of the complex indicating a positive diagnosis of Lyme borreliosis.

4. A bioassay for the diagnosis of Lyme borreliosis comprising the steps of:

i) coating a surface with at least one recombinant non-flagellar *Borrelia burgdorferi* protein wherein said protein, is specifically immunoreactive with *Borrelia burgdorferi*, and is expressed from a *Borrelia burgdorferi* DNA fragment having SEQ ID No. 1, and forming a coated surface;

ii) contacting said coated surface with serum from a mammal suspected of having Lyme disease; and iii) detecting the presence or absence of a complex formed between said protein and antibodies specific therefor present in said serum, the presence of the complex indicating a positive diagnosis of Lyme borreliosis.

5. The bioassay according to claim 4 wherein said recombinant protein is at least one of P39α protein expressed from a *Borrelia burgdorferi* DNA fragment having SEQ. ID No. 2 or P39β protein expressed from a *Borrelia burgdorferi* DNA fragment having SEQ. ID No. 3.

6. The bioassay according to claim 4, wherein said surface is a gel, a slide, membrane or a microtitration plate.

7. The bioassay according to claim 4, wherein the DNA fragment SEQ ID no. 1 expresses P39α and P39β.

8. A bioassay for the diagnosis of Lyme borreliosis comprising the steps of:

i) contacting a surface coated with purified antibodies raised against at least one recombinant non-flagellar *Borrelia burgdorferi* protein having a molecular weight of about 39 kD, wherein said protein is specifically immunoreactive with *Borrelia burgdorferi*, and is expressed from a *Borrelia burgdorferi* DNA fragment having SEQ. ID No: 1, with serum from a mammal suspected of having Lyme disease; and ii) detecting the presence or absence of a complex formed between said antibodies and proteins present in said serum, the presence of the complex indicating a positive diagnosis of Lyme borreliosis.

9. A bioassay according to claim 8 wherein said surface is coated with purified antibodies raised using at least one recombinant non-flagellar *Borrelia burgdorferi* protein having a molecular weight of about 39 kD, wherein said protein is specifically immunoreactive with antibodies produced *from Borrelia burgdorferi* antigens, and is expressed from a *Borrelia burgdorferi* DNA fragment having SEQ. ID No. 2 or 3.

10. The bioassay according to claim 8, wherein said surface is coated with purified antibodies raised using at least one recombinant non-flagellar *Borrelia burgdorferi* protein, wherein said protein is specifically immunoreactive with *Borrelia burgdorferi*, and is expressed from a *Borrelia burgdorferi* DNA fragment of pSPR33 having ATCC No. 68243.

11. A bioassay for the diagnosis of Lyme borreliosis disease comprising the steps of:

i) contacting a surface coated with at least one recombinant non-flange *Borrelia burgdorferi* protein wherein said protein is specifically immunoreactive with *Borrelia burgdorferi*, and is expressed from a *Borrelia burgdorferi* DNA fragment having SEQ ID NO: 1, with serum from a mammal suspected of having Lyme disease; and ii) detecting the presence or absence of a complex formed between said protein and antibodies specific therefor present in said serum, the presence of the complex indicating a positive diagnosis of Lyme borreliosis.

12. The bioassay according to claim 11, wherein said surface is coated with at least one recombinant non-flagellar *Borrelia burgdorferi* protein, wherein said protein is specifically immunoreactive with antibodies produced from *Borrelia burgdorferi* antigens, and is expressed from a *Borrelia burgdorferi* DNA fragment having SEQ. ID No. 2 or 3.

13. The bioassay according to claim 11, wherein said surface is coated with at least one recombinant non-flagellar *Borrelia burgdorferi* protein, wherein said protein is specifically immunoreactive with *Borrelia burgdorferi*, and is expressed from a *Borrelia burgdorferi* DNA fragment of pSPR33 having ATCC No. 68243.

14. A kit for diagnosing Lyme borreliosis comprising a recombinant non-flagellar *Borrelia burgdorferi* protein having a molecular weight of about 39 kD and ancillary reagents suitable for detecting the presence of antibodies to said protein in a mammalian serium sample.

15. The diagnostic kit according to claim 14 wherein said protein is P39α or P39β.

16. A composition comprising a recombinant non-flagellar *Borrelia burgdorferi* protein hating a molecular weight of about 39 kD bound to a solid support, wherein said protein is expressed from a *Borrelia burgdorferi* DNA fragment having SEQ ID NO: 1.

17. A composition comprising a purified antibody bound to a solid support, said purified antibody being specific for a recombinant non-flagellar *Borrelia burgdorferi* protein having a molecular weight of about 39 kD, wherein said protein is expressed from a *Borrelia burgdorferi* DNA fragment having SEQ ID NO: 1.

* * * * *